US009447075B2

(12) United States Patent
Cuny et al.

(10) Patent No.: US 9,447,075 B2
(45) Date of Patent: Sep. 20, 2016

(54) PYRIDAZINE DERIVATIVES AS EAAT2 ACTIVATORS

(75) Inventors: Gregory D. Cuny, Houston, TX (US); Marcie Glicksman, Winchester, MA (US); Xeuchao Xing, Wilmington, MA (US); Chien-Liang Glenn Lin, Columbus, OH (US)

(73) Assignees: The Brigham and Women's Hospital, Inc., Boston, MA (US); The Ohio State University, Columbus, OH (US)

( * ) Notice: Subject to any disclaimer, the term of this patent is extended or adjusted under 35 U.S.C. 154(b) by 0 days.

(21) Appl. No.: 14/236,041

(22) PCT Filed: Aug. 2, 2012

(86) PCT No.: PCT/US2012/049311
§ 371 (c)(1),
(2), (4) Date: Jun. 23, 2014

(87) PCT Pub. No.: WO2013/019938
PCT Pub. Date: Feb. 7, 2013

(65) Prior Publication Data
US 2014/0303174 A1    Oct. 9, 2014

Related U.S. Application Data

(60) Provisional application No. 61/514,347, filed on Aug. 2, 2011.

(51) Int. Cl.
*A61K 31/50* (2006.01)
*A61K 31/501* (2006.01)
*C07D 401/14* (2006.01)
*C07D 401/04* (2006.01)
*C07D 237/18* (2006.01)
*C07D 213/32* (2006.01)

(52) U.S. Cl.
CPC ............ *C07D 401/14* (2013.01); *A61K 31/50* (2013.01); *A61K 31/501* (2013.01); *C07D 213/32* (2013.01); *C07D 237/18* (2013.01); *C07D 401/04* (2013.01)

(58) Field of Classification Search
None
See application file for complete search history.

(56) References Cited

U.S. PATENT DOCUMENTS

| 4,242,512 | A | 12/1980 | Takaya et al. | |
| 6,166,020 | A * | 12/2000 | Howard et al. | 514/253.04 |
| 7,560,551 | B2 * | 7/2009 | Cee et al. | 544/237 |
| 2009/0318429 | A1 * | 12/2009 | Doyle | A61K 31/4164 |
| | | | | 514/225.2 |

FOREIGN PATENT DOCUMENTS

| FR | EP 382634 | * 8/1990 | ............ C07D 237/20 |
| WO | 98/046574 | 10/1998 | |
| WO | 2007/127475 | 11/2007 | |
| WO | 2007/130383 | 11/2007 | |
| WO | 2010/005572 | 1/2010 | |

OTHER PUBLICATIONS

Annalen der Chemie, Justus Liebigs (1941), 548, 74-81.*
Baxter, et. al., Angewandte Chemie (1994), 106(22), 2432-4.*
Pozgan, et. al., Heterocycles (2006), 70, 235-248.*
Garfunkle, Joie et al. Optimization ofthe Central Heterocycle of a-Ketoheterocycle Inhibitors of Fatty Acid Amide Hydrolase. Journal of Medicinal Chemistry, 2008, 51(15), pp. 4392-4403.
Cho, Su-Dong et al. Suzuki-Miyaura coupling reaction of aryl chlorides using di(2,6-dimethylmorpholino)phenylphosphine as ligand. Tetrahedron, 2006,63(6), pp. 1345-1352.
Stiefl, Nikolaus et al. Structure-Based Validation ofthe 3D-QSAR Technique MaP. Journal of Chemical Information and Modeling, 2005,45(3), pp. 739-749.
Yin, Zhiwei et al. Acetonitrile derivatives as carbonyl synthons. One-pot preparation of diheteroaryl ketones via a strategy of sequential SNAr substitution and oxidation. Journal of Organic Chemistry, 2004, 69(4), pp. 1364-1367.
Parrot, Isabelle et al. Efficient palladium-catalyzed amination and alkylation of 3-iodo-6-arylpyridazines. Synlett, 2002,7, pp. 1123-1127.
Jahine, H. et al. Synthesis and reactions of some 3(2H)-pyridazinethiones. Pakistan journal of Scientific Research, 1980, 32(1-2), pp. 91-95.
Rao, K. Rama et al. Synthesis and elecfron impact studies of 3-aralkylamino-6-arylpyridazines. Indian Journal of Chemistry, Section B: Organic Chemistry Including Medicinal Chemistry, 1976, 14B(II), pp. 896-897.
International Search Report and Written Opinion mailed Dec. 13, 2012 in International Application No. PCT/US2012/049311, 19 pgs.
International Preliminary Report on Patentability in International Application No. PCT/US2012/049311, mailed Feb. 13, 2014, 9 pages.
Chang et al., "Messenger RNA oxidation occurs early in disease pathogenesis and promotes motor neuron degeneration in ALS," PLoS One, 2008, 3:e2849, 19 pages.
Chen et al., "Presynaptic glutamatergic dysfunction in bipolar disorder," Biol Pshychiatry, 2010, 67(11):1007-1009 (Author Manuscript).
Chizh et al., "Novel approaches to targeting glutamate receptors for the treatment of chronic pain: review article," Amino Acids, 2002, 23(1-3):169-76.
Coates and McKillop, "One-Pot Preparation of 6-Substituted 3(2H)-Pyridazinones from Ketones," Synthesis, 1993, 3:334-342.
Colton et al., "Identification of translational activators of glial glutamate transporter EAAT2 through cell-based high-throughput screening: an approach to prevent excitotoxicity," J Biomol Screen. 2010, 15(6):653-62.

(Continued)

*Primary Examiner* — Jeffrey H Murray
(74) *Attorney, Agent, or Firm* — Fish & Richardson P.C.

(57) ABSTRACT

Pyridazine derivatives that activate the excitatory amino acid transporter 2 (EAAT2), and methods use thereof for treating or preventing diseases, disorders, and conditions associated with glutamate excitotoxicity.

16 Claims, 18 Drawing Sheets

(56) References Cited

OTHER PUBLICATIONS

Descalzi et al., "Presynaptic and postsynaptic cortical mechanisms of chronic pain," Mol Neurobiol., 2009, 40(3):253-9.

Ghiron et al., "Novel alpha-7 nicotinic acetylcholine receptor agonists containing a urea moiety: identification and characterization of the potent, selective, and orally efficacious agonist 1-[6-(4-fluorophenyl)pyridin-3-y1]-3-(4-piperidin-1-ylbutyl) urea (SEN34625/WYE-103914),"J Med Chem., 2010, 53(11):4379-89.

Guo et al., "Increased expression of the glial glutamate transporter EAAT2 modulates excitotoxicity and delays the onset but not the outcome of ALS in mice," Hum Mol Genet. 2003, 12:2519-32.

Hazell, "Excitotoxic mechanisms in stroke: an update of concepts and treatment strategies," Neurochem. Int., 2007 50:941-53.

Hu et al., "Glutamate receptors in preclinical research on Alzheimer's disease: Update on recent advances," Pharmacol Biochem Behav., Apr. 22, 2011 100(4):855-62.

Kaul and Lipton, "Mechanisms of neuronal injury and death in HIV-1 associated dementia," Curr HIV Res., 2006, 4(3):307-18.

Kim et al., "Role of excitatory amino acid transporter-2 (EAAT2) and glutamate in neurodegeneration: opportunities for developing novel therapeutics," J Cell Physiol., 2011, 226(10):2484-93 (Author Manuscript).

Knapp et al., "A general solution for unstable boronic acids: slow-release cross-coupling from air-stable MIDA boronates," J Am Chem Soc., 2009, 131:6961.

Kong et al., "Increased glial glutamate transporter EAAT2 expression reduces epileptogenic processes following pilocarpine-induced status epilepticus," Neurobiol Dis., 2012, 47(2):145-54.

Larsson, "Ionotropic glutamate receptors in spinal nociceptive processing," Mol Neurobiol., 2009, 40(3):260-88.

Lin et al., "Increased glial glutamate transporter EAAT2 expression reduces visceral nociceptive response in mice," Am J Physiol Gastrointest Liver Physiol., 2009, 296:G129-G134.

Ludolph et al., "Guidelines for the preclinical in vivo evaluation of pharmacological active drugs for ALS/MND: report on the 142nd ENMC international workshop," Amyotroph Lateral Scler., 2007, 8:217-223.

Mark et al., "Pictorial review of glutamate excitotoxicity: fundamental concepts for neuroimaging," Am J Neuroradiol., 2001, 22:1813-1824.

Myers et al., "Glutamate receptors in extinction and extinction-based therapies for psychiatric illness," Neuropsychopharmacol., 2011, 36(1):274-93.

Nakatsu et al., "Glutamate excitotoxicity is involved in cell death caused by tributyltin in cultured rat cortical neurons," Toxicol Sci., Jan. 2006, 89(1): 235-242.

Noch and Khalili, "Molecular mechanisms of necrosis in glioblastoma: the role of glutamate excitotoxicity," Cancer Biol Ther., 2009, 8(19):1791-7 (Author Manuscript).

Olney, "Neurotoxicity of excitatory amino acids," In: Kainic Acid as a Tool in Neurobiology. New York: Raven Press; 1978, pp. 95-121.

Olney, "Role of excitotoxins in developmental neuropathology," APMIS Suppl 40, 1993 101:103-112.

Owen, "Glutamatergic approaches in major depressive disorder: focus on ketamine, memantine and riluzole," Drugs Today (Barc), 2012, 48(7):469-78.

Prost et al., "Detection of glutamate/glutamine resonances by 1H magnetic resonance spectroscopy at 0.5 tesla," Magn Reson Med., 1997, 37:615-618.

Racine, "Modification of seizure activity by electrical stimulation. II. Motor seizure," Electroencephalogr Clin Neurophysiol., 1972, 32:281-294.

Reissner and Kalivas, "Using glutamate homeostasis as a target for treating addictive disorders," Behav Pharmacol. Sep. 2010, 21(5-6):514-22.

Seifert et al., "Astrocyte dysfunction in epilepsy," Brain Res Rev., 2010, 63:212-21.

Shapiro et al., "Newly generated granule cells show rapid neuroplastic changes in the adult rat dentate gyrus during the first five days following pilocarpine-induced seizures," Eur J Neurosci., 2007, 26:583-592.

Sheldon and Robinson, "The role of glutamate transporters in neurodegenerative diseases and potential opportunities for intervention," Neurochem Int., 2007, 51(6-7):333-55 (Author Manuscript).

Tian et al., "Increased expression of cholesterol 24S-hydroxylase results in disruption of glial glutamate transporter EAAT2 association with lipid rafts: a potential role in Alzheimer's disease," J. Neurochem., 2010, 113:978-89.

Tian et al., "Translational control of glial glutamate transporter EAAT2 expression," J Biol Chem., 2007, 282:1727-37.

Tzschentke, "Glutamatergic mechanisms in different disease states: overview and therapeutical implications mplications—an introduction," Amino Acids, 2002, 23(1-3):147-52.

Vargas, "Chronic migraine: current pathophysiologic concepts as targets for treatment," Curr Pain Headache Rep., 2009, 13(1):64-6.

Wang and Qin, "Molecular and cellular mechanisms of excitotoxic neuronal death," Apoptosis., 2010, 15(11):1382-402.

Yogeswaari et al., "Current approaches with the glutamatergic system as targets in the treatment of neuropathic pain," Expert Opin Ther Targets, 2009, 13(8):925-43.

\* cited by examiner

1: 
¹H NMR (500 Hz, CDCl₃) δ 8.69 (m, 1H), 8.66 (d, *J* = 7.5 Hz, 1H), 8.38 (d, *J* = 9.0 Hz, 1H), 7.87 (td, *J* = 1.5, 7.5 Hz, 1H), 7.45 (d, *J* = 9.0 Hz, 1H), 7.38 (m, 1H), 7.24 (m, 2H), 7.03 (m, 1H), 4.92 (d, *J* = 2.0 Hz, 2H).

5-1: 
¹H NMR (500 Hz, DMSO-d₆) δ 13.29 (s, 1H), 8.66 (m, 1H), 8.29 (d, *J* = 9.5 Hz, 1H), 8.06 (m, 1H), 7.93 (td, *J* = 2.0, 7.5 Hz, 1H), 7.46 (dd, *J* = 1.5, 5.0 Hz, 1H), 7.02 (d, *J* = 9.5 Hz, 1H).

6-1: 
¹H NMR (500 Hz, DMSO-d₆) δ 14.98 (s, 1H), 8.72 (d, *J* = 5.0 Hz, 1H), 8.12 (t, *J* = 4.0 Hz, 2H), 7.93 (td, *J* = 2.0, 8.0 Hz, 1H), 7.46 (dd, *J* = 2.0, 10.0 Hz, 1H), 7.53 (m, 1H).

7-4: 
¹H NMR (500 Hz, CDCl₃) δ 8.69 (d, *J* = 5.0 Hz, 1H), 8.64 (d, *J* = 8.0 Hz, 1H), 8.35 (d, *J* = 8.5 Hz, 1H), 7.87 (td, *J* = 1.5, 8.0 Hz, 1H), 7.43 (m, 2H), 7.37 (m, 1H), 7.18 (m, 3H), 4.19 (s, 2H), 2.46 (s, 3H).

7-5: 
¹H NMR (500 Hz, CDCl₃) δ 9.22 (d, *J* = 1.5 Hz, 1H), 8.73 (dd, *J* = 1.5, 5.0 Hz, 1H), 7.95 (dt, *J* = 2.0, 7.5 Hz, 1H), 7.69 (d, *J* = 9.5 Hz, 1H), 7.47 (m, 1H), 7.44 (d, *J* = 7.5 Hz, 1H), 7.41 (d, *J* = 9.0 Hz, 1H), 7.15-7.23 (m, 3H), 4.71 (s, 2H), 2.46 (s, 3H).

7-6: 
¹H NMR (500 Hz, CDCl₃) δ 8.06 (m, 2H), 7.66 (d, *J* = 9.5 Hz, 1H), 7.51 (m, 3H), 7.44 (d, *J* = 7.0 Hz, 1H), 7.36 (d, *J* = 8.5 Hz, 1H), 7.18 (m, 3H), 4.71 (s, 2H), 2.46 (s, 3H).

7-7: 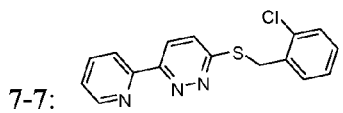
¹H NMR (500 Hz, CDCl₃) δ 8.69 (m, 1H), 8.63 (d, $J$ = 8.0 Hz, 1H), 8.35 (d, $J$ = 9.0 Hz, 1H), 7.87 (td, $J$ = 1.5, 7.5 Hz, 1H), 7.64 (m, 1H), 7.43 (d, $J$ = 9.0 Hz, 1H), 7.39 (m, 2H), 7.22 (m, 2H), 4.83 (s, 2H).

7-8: 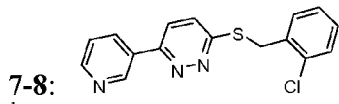
¹H NMR (500 Hz, CDCl₃) δ 9.21 (d, $J$ = 2.5 Hz, 1H), 8.73 (dd, $J$ = 1.5, 5.0 Hz, 1H), 8.32 (dt, $J$ = 2.0, 8.0 Hz, 1H), 7.68 (d, $J$ = 9.0 Hz, 1H), 7.65 (m, 1H), 7.47 (dd, $J$ = 4.5, 7.5 Hz, 1H), 7.42 (d, $J$ = 8.5 Hz, 1H), 7.40 (m, 1H), 7.22 (m, 2H), 4.82 (s, 2H).

7-9: 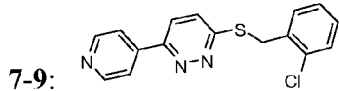
¹H NMR (500 Hz, CDCl₃) δ 8.79 (dd, $J$ = 2.0, 6.0 Hz, 2H), 7.95 (dd, $J$ = 2.0, 6.5 Hz, 2H), 7.69 (d, $J$ = 9.0 Hz, 1H), 7.65 (m, 1H), 7.43 (d, $J$ = 9.5 Hz, 1H), 7.40 (m, 1H), 7.22 (m, 2H), 4.83 (s, 2H).

7-12: 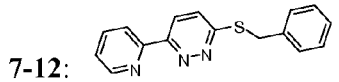
¹H NMR (500 Hz, CDCl₃) δ 8.69 (m, 1H), 8.63 (d, $J$ = 8.0 Hz, 1H), 8.35 (d, $J$ = 9.0 Hz, 1H), 7.86 (td, $J$ = 2.0, 8.0 Hz, 1H), 7.48 (d, $J$ = 7.5 Hz, 2H), 7.43 (d, $J$ = 9.5 Hz, 1H), 7.38 (m, 1H), 7.34 (t, $J$ = 7.5 Hz, 2H), 7.27 (m, 1H), 4.70 (s, 2H).

7-13: 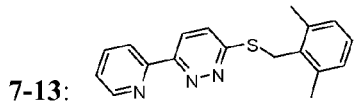
¹H NMR (500 Hz, CDCl₃) δ 8.70 (m, 1H), 8.66 (dd, $J$ = 1.0, 7.5 Hz, 1H), 8.35 (d, $J$ = 9.0 Hz, 1H), 7.87 (td, $J$ = 2.0, 7.5 Hz, 1H), 7.45 (d, $J$ = 8.5 Hz, 1H), 7.38 (m, 1H), 7.14-7.06 (m, 3H), 4.76 (s, 2H), 2.47 (s, 6H).

FIG. 1

7-14: 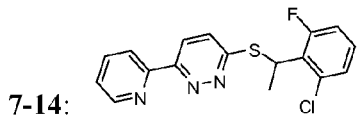

¹H NMR (500 Hz, CDCl₃) δ 8.68 (dd, $J$ = 1.0, 5.0 Hz, 1H), 8.66 (d, $J$ = 8.0 Hz, 1H), 8.35 (d, $J$ = 9.0 Hz, 1H), 7.87 (td, $J$ = 2.0, 8.0 Hz, 1H), 7.40 (d, $J$ = 9.0 Hz, 1H), 7.37 (m, 1H), 7.19 (m, 2H), 7.03 (m, 1H), 6.28 (q, $J$ = 7.0 Hz, 1H), 1.94 (d, $J$ = 7.5 Hz, 3H).

7-15: 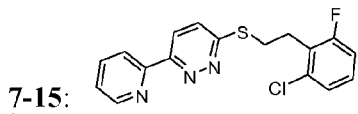

¹H NMR (500 Hz, CDCl₃) δ 8.69 (m, 1H), 8.64 (d, $J$ = 8.5 Hz, 1H), 8.35 (d, $J$ = 9.5 Hz, 1H), 7.86 (td, $J$ = 1.5, 7.5 Hz, 1H), 7.44 (d, $J$ = 9.5 Hz, 1H), 7.37 (m, 1H), 7.16 (m, 2H), 6.97 (m, 1H), 3.70 (t, $J$ = 7.0 Hz, 2H), 3.35 (td, $J$ = 2.0, 7.0 Hz, 2H).

7-16: 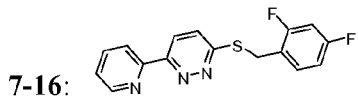

¹H NMR (500 Hz, CDCl₃) δ 8.69 (m, 1H), 8.62 (m, 1H), 8.36 (d, $J$ = 9.0 Hz, 1H), 7.87 (td, $J$ = 1.5, 8.0 Hz, 1H), 7.56 (m, 1H), 7.43 (d, $J$ = 9.5 Hz, 1H), 7.38 (m, 1H), 6.82 (m, 2H), 4.69 (s, 2H).

7-17: 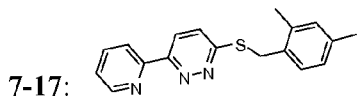

¹H NMR (500 Hz, CDCl₃) δ 8.69 (m, 1H), 8.64 (d, $J$ = 8.0 Hz, 1H), 8.35 (d, $J$ = 9.0 Hz, 1H), 7.87 (td, $J$ = 2.0, 8.0 Hz, 1H), 7.42 (d, $J$ = 8.5 Hz, 1H), 7.37 (m, 1H), 7.33 (d, $J$ = 7.5 Hz, 1H), 7.03 (s, 1H), 6.98 (d, $J$ = 7.5 Hz, 1H), 4.69 (s, 2H), 2.42 (s, 3H), 2.31 (s, 3H).

7-18: 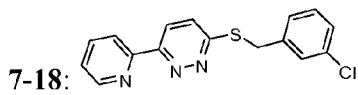

¹H NMR (500 Hz, CDCl₃) δ 8.69 (m, 1H), 8.63 (d, $J$ = 1.0, 8.0 Hz, 1H), 8.36 (d, $J$ = 8.0 Hz, 1H), 7.86 (td, $J$ = 2.0, 8.0 Hz, 1H), 7.48 (s, 1H), 7.43 (d, $J$ = 10.0 Hz, 1H), 7.37 (m, 2H), 7.24 (m, 2H), 4.66 (s, 2H).

7-19: 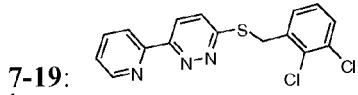

¹H NMR (500 Hz, CDCl₃) δ 8.69 (d, $J$ = 4.5 Hz, 1H), 8.62 (d, $J$ = 7.5 Hz, 1H), 8.35 (d, $J$ = 9.0 Hz, 1H), 7.87 (td, $J$ = 1.5, 7.5 Hz, 1H), 7.59 (dd, $J$ = 1.5, 7.5 Hz, 1H), 7.43 (d, $J$ = 9.5 Hz, 1H), 7.37 (m, 2H), 7.14 (t, $J$ = 8.0 Hz, 1H), 4.85 (s, 2H).

FIG. 1

7-20: 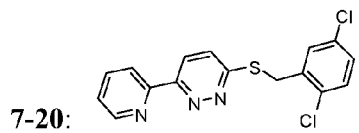
¹H NMR (500 Hz, CDCl₃) δ 8.69 (d, $J$ = 5.0 Hz, 1H), 8.63 (d, $J$ = 8.5 Hz, 1H), 8.37 (d, $J$ = 9.5 Hz, 1H), 7.87 (td, $J$ = 2.0, 8.0 Hz, 1H), 7.65(d, $J$ = 2.5 Hz, 1H), 7.44 (d, $J$ = 9.0 Hz, 1H), 7.38 (dd, $J$ = 4.5, 7.5 Hz, 1H), 7.33 (d, $J$ = 8.0 Hz, 1H), 7.19 (dd, $J$ = 2.0, 8.0 Hz, 1H), 4.79 (s, 2H).

7-21: 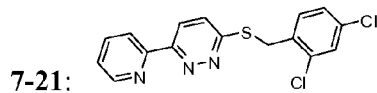
¹H NMR (500 Hz, CDCl₃) δ 8.69 (d, $J$ = 5.0 Hz, 1H), 8.62 (d, $J$ = 7.5 Hz, 1H), 8.35 (d, $J$ = 9.0 Hz, 1H), 7.87 (td, $J$ = 1.5, 8.0 Hz, 1H), 7.61 (d, $J$ = 8.5 Hz, 1H), 7.42 (m, 2H), 7.37 (m, 1H), 7.19 (dd, $J$ = 2.0, 8.5 Hz, 1H), 4.78 (s, 2H).

7-22: 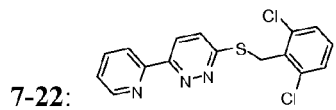
¹H NMR (500 Hz, CDCl₃) δ 8.70 (m, 1H), 8.66 (d, $J$ = 8.0 Hz, 1H), 8.38 (d, $J$ = 9.5 Hz, 1H), 7.87 (td, $J$ = 2.0, 8.0 Hz, 1H), 7.47 (d, $J$ = 8.5 Hz, 1H), 7.38 (m, 1H), 7.35 (d, $J$ = 8.5 Hz, 2H), 7.12 (t, $J$ = 8.0 Hz, 1H), 5.07 (s, 2H).

7-25: 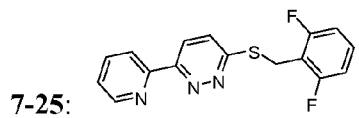
¹H NMR (500 Hz, CDCl₃) δ 8.69 (m, 1H), 8.65 (d, $J$ = 7.5 Hz, 1H), 8.38 (d, $J$ = 9.5 Hz, 1H), 7.87 (td, $J$ = 2.0, 8.0 Hz, 1H), 7.45 (d, $J$ = 9.0 Hz, 1H), 7.38 (m, 1H), 7.26 (m, 1H), 6.93(m, 2H), 4.81 (s, 2H).

7-26: 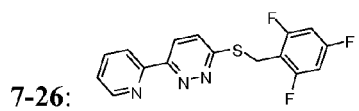
¹H NMR (500 Hz, CDCl₃) δ 8.70 (m, 1H), 8.65 (d, $J$ = 7.5 Hz, 1H), 8.39 (d, $J$ = 9.0 Hz, 1H), 7.88 (td, $J$ = 1.5, 8.0 Hz, 1H), 7.44 (d, $J$ = 9.5 Hz, 1H), 7.39 (m, 1H), 6.70(m, 2H), 4.76 (s, 2H).

FIG. 1

7-27: 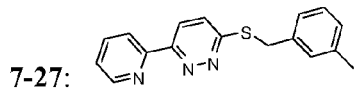
¹H NMR (500 Hz, CDCl₃) δ 8.69 (d, $J$ = 4.5 Hz, 1H), 8.63 (d, $J$ = 8.0 Hz, 1H), 8.35 (d, $J$ = 9.0 Hz, 1H), 7.86 (td, $J$ = 2.0, 8.0 Hz, 1H), 7.42 (d, $J$ = 9.0 Hz, 1H), 7.37 (m, 1H), 7.28 (m, 2H), 7.22 (t, $J$ = 7.5 Hz, 1H), 7.09 (d, $J$ = 7.5 Hz, 1H), 4.66 (s, 2H), 2.35 (s, 3H).

7-29: 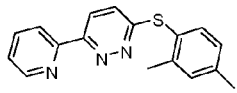
¹H NMR (500 Hz, CDCl₃) δ 8.65 (m, 1H), 8.61 (d, $J$ = 8.0 Hz, 1H), 8.27 (d, $J$ = 9.0 Hz, 1H), 7.83 (td, $J$ = 2.0, 7.5 Hz, 1H), 7.53 (d, $J$ = 8.0 Hz, 1H), 7.65 (ddd, $J$ = 1.0, 5.0, 7.5 Hz, 1H), 7.21 (s, 1H), 7.10 (dd, $J$ = 1.5, 7.5 Hz, 1H), 7.02 (d, $J$ = 9.0 Hz, 1H), 2.39 (s, 6H).

7-30: 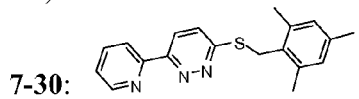
¹H NMR (500 Hz, CDCl₃) δ 8.69 (m, 1H), 8.65 (d, $J$ = 7.5 Hz, 1H), 8.37 (d, $J$ = 9.0 Hz, 1H), 7.87 (td, $J$ = 2.0, 8.0 Hz, 1H), 7.45 (d, $J$ = 9.5 Hz, 1H), 7.37 (m, 1H), 6.90 (s, 2H), 4.73 (s, 2H), 2.43 (s, 6H), 2.29 (s, 3H).

7-31: 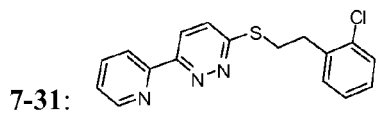
¹H NMR (500 Hz, CDCl₃) δ 8.69 (m, 1H), 8.63 (d, $J$ = 8.5 Hz, 1H), 8.35 (d, $J$ = 9.0 Hz, 1H), 7.87 (td, $J$ = 2.0, 8.0 Hz, 1H), 7.44 (d, $J$ = 9.5 Hz, 1H), 7.37 (m, 3H), 7.18 (m, 2H), 3.71 (t, $J$ = 7.5 Hz, 2H), 3.28 (t, $J$ = 7.5 Hz, 2H).

7-32: 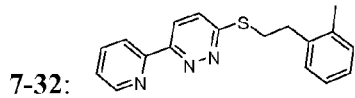
¹H NMR (500 Hz, CDCl₃) δ 8.69 (m, 1H), 8.63 (d, $J$ = 8.0 Hz, 1H), 8.34 (d, $J$ = 9.5 Hz, 1H), 7.86 (td, $J$ = 2.0, 8.0 Hz, 1H), 7.43 (d, $J$ = 9.0 Hz, 1H), 7.37 (m, 1H), 7.27 (m, 1H), 7.16 (m, 3H), 3.65 (t, $J$ = 7.5 Hz, 2H), 3.14 (t, $J$ = 7.5 Hz, 2H), 2.39 (s, 3H).

FIG. 1

7-33: 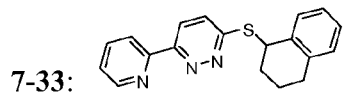

¹H NMR (500 Hz, CDCl$_3$) δ 8.70 (m, 1H), 8.66 (d, $J$ = 8.0 Hz, 1H), 8.37 (d, $J$ = 9.5 Hz, 1H), 7.87 (td, $J$ = 1.5, 7.5 Hz, 1H), 7.46 (m, 1H), 7.39 (d, $J$ = 9.0 Hz, 1H), 7.37 (m, 1H), 7.11-7.19 (m, 3H), 5.79 (t, $J$ = 4.0 Hz, 1H), 2.85 (m, 2H), 2.35 (m, 2H), 2.13 (m, 1H), 1.93 (m, 1H).

7-34: 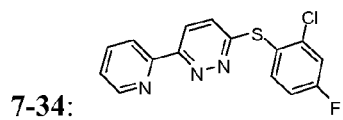

¹H NMR (500 Hz, CDCl$_3$) δ 8.67 (m, 1H), 8.61 (d, $J$ = 7.5 Hz, 1H), 8.39 (d, $J$ = 8.5 Hz, 1H), 7.84 (td, $J$ = 1.5, 7.5 Hz, 1H), 7.78 (dd, $J$ = 6.0, 9.0 Hz, 1H), 7.35 (m, 2H), 7.28 (d, $J$ = 9.0 Hz, 1H), 7.10 (m, 1H).

7-35: 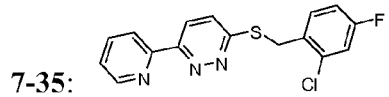

¹H NMR (500 Hz, CDCl$_3$) δ 8.69 (d, $J$ = 5.0 Hz, 1H), 8.62 (d, $J$ = 8.0 Hz, 1H), 8.35 (d, $J$ = 9.0 Hz, 1H), 7.87 (td, $J$ = 2.0, 7.5 Hz, 1H), 7.65 (dd, $J$ = 6.0, 9.0 Hz, 1H), 7.42 (d, $J$ = 8.5 Hz, 1H), 7.38 (m, 1H), 7.15 (dd, $J$ = 2.5, 8.5 Hz, 1H), 6.92 (td, $J$ = 3.0, 8.0 Hz, 1H), 4.78 (s, 2H).

7-36: 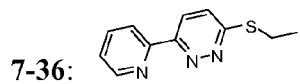

¹H NMR (500 Hz, CDCl$_3$) δ 8.68 (m, 1H), 8.63 (d, $J$ = 8.0 Hz, 1H), 8.34 (d, $J$ = 9.0 Hz, 1H), 7.85 (td, $J$ = 2.0, 7.5 Hz, 1H), 7.43 (d, $J$ = 9.0 Hz, 1H), 7.36 (m, 1H), 3.43 (q, $J$ = 7.5 Hz, 2H), 1.49 (t, $J$ = 7.5 Hz, 3H).

8-1: 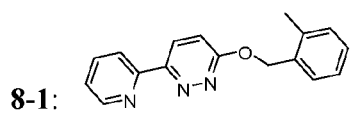

¹H NMR (500 Hz, CDCl$_3$) δ 8.61 (d, $J$ = 5.0 Hz, 1H), 8.34 (d, $J$ = 10.0 Hz, 1H), 8.01 (d, $J$ = 7.5 Hz, 1H), 7.74 (td, $J$ = 2.0, 8.0 Hz, 1H), 7.29 (m, 2H), 7.15-7.21 (m, 3H), 7.06 (d, $J$ = 10.0 Hz, 1H), 5.45 (s, 2H), 2.50 (s, 3H).

FIG. 1

8-2: 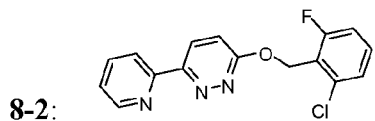
¹H NMR (500 Hz, CDCl₃) δ 8.57 (m, 1H), 8.31 (d, $J$ = 9.5 Hz, 1H), 7.77 (m, 1H), 7.68 (m, 1H), 7.32-7.23 (m, 3H), 7.07 (m, 1H), 7.04 (d, $J$ = 9.5 Hz, 1H), 5.60 (d, $J$ = 1.5 Hz, 2H).

8-3: 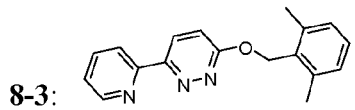
¹H NMR (500 Hz, CDCl₃) δ 8.56 (m, 1H), 8.29 (d, $J$ = 10.0 Hz, 1H), 7.63-7.67 (m, 2H), 7.22 (m, 1H), 7.16 (dd, $J$ = 7.0, 8.0 Hz, 1H), 7.09 (d, $J$ = 8.0 Hz, 2H), 7.05 (d, $J$ = 10.0 Hz, 1H), 5.48 (s, 2H), 2.41 (s, 6H).

8-4: 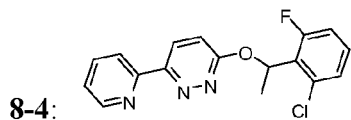
¹H NMR (500 Hz, CDCl₃) δ 8.61 (dd, $J$ = 1.5, 4.5 Hz, 1H), 8.34 (d, $J$ = 10.0 Hz, 1H), 8.08 (d, $J$ = 8.5 Hz, 1H), 7.26 (td, $J$ = 2.0, 7.5 Hz, 1H), 7.29 (m, 1H), 7.20 (m, 2H), 6.98 (m, 2H), 6.55 (q, $J$ = 7.0 Hz, 1H), 2.46 (dd, $J$ = 2.0, 7.0 Hz, 3H).

8-5: 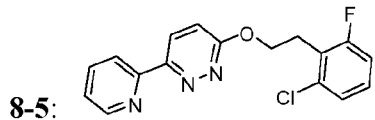
¹H NMR (500 Hz, CDCl₃) δ 8.60 (d, $J$ = 5.0 Hz, 1H), 8.29 (d, $J$ = 10.0 Hz, 1H), 7.70 (m, 2H), 7.28 (dd, $J$ = 1.5, 5.0 Hz, 1H), 7.12 (m, 2H), 7.00 (d, $J$ = 10.0 Hz, 1H), 6.92 (td, $J$ = 1.5, 9.0 Hz, 1H), 4.54 (t, $J$ = 7.0 Hz, 2H), 4.39 (td, $J$ = 1.5, 7.0 Hz, 2H).

8-6: 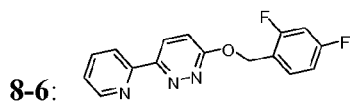
¹H NMR (500 Hz, CDCl₃) δ 8.61 (m, 1H), 8.34 (d, $J$ = 10.0 Hz, 1H), 8.07 (d, $J$ = 7.0 Hz, 1H), 7.78 (td, $J$ = 2.0, 8.0 Hz, 1H), 7.22 (dd, $J$ = 8.0, 10.0 Hz, 1H), 7.30 (m, 1H), 7.04 (d, $J$ = 10.0 Hz, 1H), 6.85 (m, 2H), 5.45 (s, 2H).

FIG. 1

8-7: 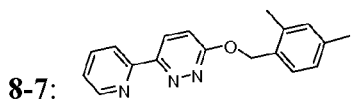
¹H NMR (500 Hz, CDCl₃) δ 8.61 (m, 1H), 8.33 (d, $J$ = 9.5 Hz, 1H), 8.03 (d, $J$ = 7.0 Hz, 1H), 7.75 (td, $J$ = 2.0, 8.0 Hz, 1H), 7.29 (m, 1H), 7.22 (d, $J$ = 8.0 Hz, 1H), 7.04 (d, $J$ = 9.5 Hz, 1H), 7.02 (s, 1H), 6.97 (d, $J$ = 8.0 Hz, 1H), 5.41 (s, 2H), 2.47 (s, 3H), 2.29 (s, 3H).

9-1: 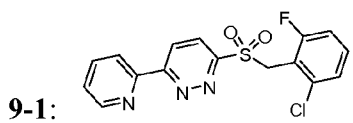
¹H NMR (500 Hz, CDCl₃) δ 8.79 (m, 3H), 8.12 (d, $J$ = 9.0 Hz, 1H), 7.87 (td, $J$ = 2.0, 8.0 Hz, 1H), 7.49 (m, 1H), 7.31 (m, 1H), 7.25 (t, $J$ = 9.0 Hz, 1H), 7.03 (t, $J$ = 9.0 Hz, 1H), 5.16 (d, $J$ = 1.5 Hz, 2H).

9-2: 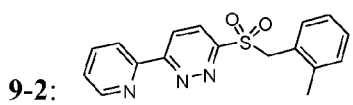
¹H NMR (500 Hz, CDCl₃) δ 8.78 (m, 3H), 8.07 (d, $J$ = 9.0 Hz, 1H), 7.95 (td, $J$ = 1.5, 8.0 Hz, 1H), 7.49 (m, 1H), 7.21 (m, 2H), 7.14 (d, $J$ = 7.5 Hz, 1H), 7.09 (m, 1H), 4.96 (s, 2H), 2.46 (s, 3H).

9-3: 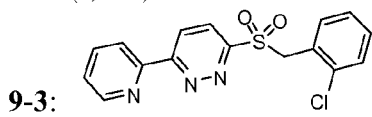
¹H NMR (500 Hz, CDCl₃) δ 8.77 (m, 3H), 8.06 (d, $J$ = 9.0 Hz, 1H), 7.96 (td, $J$ = 1.5, 8.0 Hz, 1H), 7.49 (m, 1H), 7.42 (d, $J$ = 7.5 Hz, 1H), 7.37 (d, $J$ = 8.0 Hz, 1H), 7.29 (t, $J$ = 7.5 Hz, 1H), 7.24 (t, $J$ = 7.5 Hz, 1H), 5.10 (s, 2H).

14: 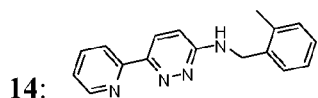
¹H NMR (500 Hz, CDCl₃) δ 8.63 (dd, $J$ = 1.0, 5.0 Hz, 1H), 8.55 (d, $J$ = 8.5 Hz, 1H), 8.29 (d, $J$ = 9.5 Hz, 1H), 7.80 (td, $J$ = 1.5, 7.5 Hz, 1H), 7.35 (d, $J$ = 7.0 Hz, 1H), 7.28 (m, 1H), 7.18-7.24 (m, 3H), 6.75 (d, $J$ = 9.5 Hz, 1H), 4.91 (s, 1H), 4.71 (d, $J$ = 5.5 Hz, 2H), 2.40 (s, 3H).

FIG. 1

15: 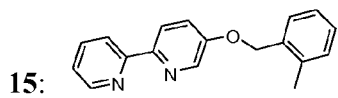
¹H NMR (500 Hz, CDCl₃) δ 8.64 (d, $J$ = 4.5 Hz, 1H), 8.44 (d, $J$ = 2.5 Hz, 1H), 8.35 (d, $J$ = 8.5 Hz, 1H), 8.31 (d, $J$ = 8.0 Hz, 1H ), 7.78 (td, $J$ = 2.0, 7.5 Hz, 1H), 7.41 (m, 2H), 7.22-7.30 (m, 4H), 5.15 (s, 2H), 2.41 (s, 3H).

16: 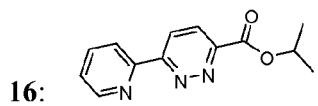
¹H NMR (500 Hz, CDCl₃) δ 8.78 (d, $J$ = 7.5 Hz, 1H), 8.74 (d, $J$ = 4.0 Hz, 1H), 8.70 (d, $J$ = 8.5 Hz, 1H), 8.28 (d, $J$ = 9.0 Hz, 1H), 7.92 (td, $J$ = 2.0, 8.0 Hz, 1H), 7.44 (m, 1H), 5.41 (hp, $J$ = 6.5 Hz, 1H), 1.48 (d, $J$ = 6.5 Hz, 6H).

17-1: 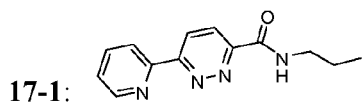
¹H NMR (500 Hz, CDCl₃) δ 8.75 (m, 2H), 8.69 (d, $J$ = 7.5 Hz, 1H), 8.43 (d, $J$ = 8.5 Hz, 1H), 8.25 (s, 1H), 7.92 (td, $J$ = 1.0, 7.5 Hz, 1H), 7.44 (dd, $J$ = 5.0, 8.0 Hz, 1H), 1H), 3.53 (q, $J$ = 6.5 Hz, 2H), 1.72 (h, $J$ = 7.5 Hz, 2H), 1.04 (t, $J$ = 7.5 Hz, 3H).

17-2: 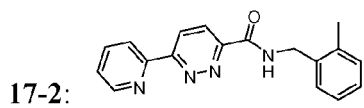
¹H NMR (500 Hz, CDCl₃) δ 8.75 (m, 2H), 8.67 (d, $J$ = 8.0 Hz, 1H), 8.45 (d, $J$ = 9.0 Hz, 1H), 8.38 (s, 1H), 7.91 (td, $J$ = 1.5, 7.5 Hz, 1H), 7.44 (m, 1H), 7.36 (d, $J$ = 7.0 Hz, 1H), 7.21 (m, 3H), 4.74 (d, $J$ = 6.0 Hz, 2H), 2.41 (s, 3H).

19: 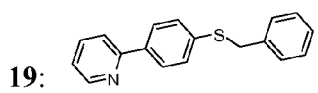
¹H NMR (500 Hz, CDCl₃) δ 8.68 (d, $J$ = 5.0 Hz, 1H), 8.39 (d, $J$ = 4.5 Hz, 1H), 7.89 (d, $J$ = 9.0 Hz, 2H), 7.68-7.76 (m, 2H), 7.55 (td, $J$ = 2.0, 8.0 Hz, 1H), 7.49 (d, $J$ = 8.0 Hz, 1H), 7.39 (d, $J$ = 8.5 Hz, 2H), 7.19-7.34 (m, 3H), 4.18 (s, 2H).

20: 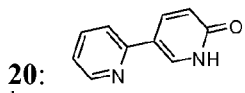
¹H NMR (500 Hz, CDCl₃) δ 12.48 (br.s, 1H), 8.61 (m, 1H), 8.18 (dd, $J$ = 3.0, 9.5 Hz, 1H), 8.13 (d, $J$ = 2.0 Hz, 1H), 7.72 (td, $J$ = 2.0, 8.0 Hz, 1H), 7.50 (d, $J$ = 8.5 Hz, 1H), 7.20 (m, 1H), 6.71 (d, $J$ = 9.0 Hz, 1H).

FIG. 1

21: 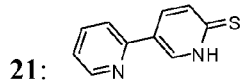

¹H NMR (500 Hz, CDCl₃) δ 13.10 (br.s, 1H), 8.65 (d, *J* = 4.5 Hz, 1H), 8.32 (d, *J* = 1.5 Hz, 1H), 8.13 (dd, *J* = 2.0, 9.0 Hz, 1H), 7.78 (td, *J* = 1.5, 8.0 Hz, 1H), 7.65 (d, *J* = 9.0 Hz, 1H), 7.59 (d, *J* = 8.5 Hz, 1H), 7.26 (m, 1H),

22: 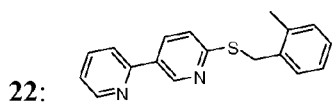

¹H NMR (500 Hz, CDCl₃) δ 9.06 (d, *J* = 2.0 Hz, 1H), 8.70 (d, *J* = 4.0 Hz, 1H), 8.15 (dd, *J* = 2.0, 8.0 Hz, 1H), 7.77 (td, *J* = 2.0, 8.0 Hz, 1H), 7.71 (d, *J* = 8.0 Hz, 1H), 7.40 (d, *J* = 8.0 Hz, 1H), 7.26 (m, 2H), 7.15 (m, 3H), 4.51 (s, 2H), 2.44 (s, 3H).

23: 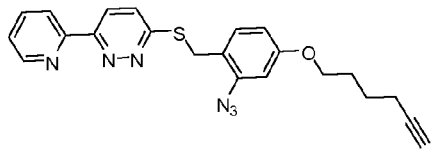

¹H NMR (500 Hz, CDCl₃) δ 8.65 (m, 1H), 8.08 (d, *J* = 9.5 Hz, 1H), 7.98 (d, *J* = 8.5 Hz, 1H), 7.94 (d, *J* = 9.0 Hz, 1H), 7.76 (td, *J* = 2.0, 8.0 Hz, 1H), 7.33 (dd, *J* = 5.0, 7.5 Hz, 1H), 7.16 (d, *J* = 9.0 Hz, 1H), 6.74 (d, *J* = 2.5 Hz, 1H), 6.63 (dd, *J* = 2.0, 8.5 Hz, 1H), 5.85 (s, 2H), 4.00 (t, *J* = 6.5 Hz, 2H), 2.28 (m, 2H), 1.90-1.97 (m, 3H), 1.72 (m, 2H).

24: 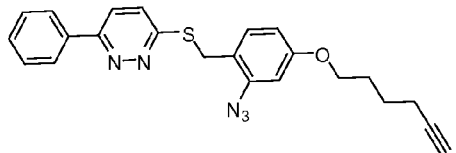

1H NMR (500 Hz, CDCl₃) δ 7.90 (d, J = 9.5 Hz, 1H), 7.75 (m, 2H), 7.45 (m, 3H), 7.40 (d, J = 9.5 Hz, 1H), 7.16 (d, J = 8.5 Hz, 1H), 6.73 (d, J = 2.5 Hz, 1H), 6.62 (dd, J = 2.5, 8.5 Hz, 1H), 5.82 (s, 2H), 4.00 (t, J = 6.5 Hz, 2H), 2.28 (m, 2H), 1.90-1.97 (m, 3H), 1.72 (m, 2H).

25: 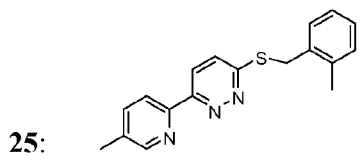

1H NMR (500 Hz, CDCl₃) δ 8.52 (m, 2H), 8.32 (d, J = 9.0 Hz, 1H), 7.68 (d, J = 8.0 Hz, 1H), 7.44 (d, J = 7.5 Hz, 1H), 7.41 (d, J = 9.0 Hz, 1H), 7.21-7.16 (m, 3H), 4.71 (s, 2H), 2.46 (s, 3H), 2.42 (s, 3H).

1H NMR (500 Hz, CDCl$_3$) δ 8.69 (d, J = 5.0 Hz, 1H), 8.62 (d, J = 8.0 Hz, 1H), 8.34 (d, J = 9.0 Hz, 1H), 7.86 (td, J = 1.5, 8.0 Hz, 1H), 7.52 (t, J = 7.5 Hz, 1H), 7.48 (d, J = 9.0 Hz, 1H), 7.38-7.35 (m, 2H), 7.04 (d, J = 7.5 Hz, 1H), 4.79 (s, 2H), 2.57 (s, 3H).

27:

1H NMR (500 Hz, CDCl$_3$) δ 8.78 (d, J = 7.5 Hz, 1H), 8.74 (d, J = 4.0 Hz, 1H), 8.70 (d, J = 8.5 Hz, 1H), 8.28 (d, J = 9.0 Hz, 1H), 7.92 (td, J = 2.0, 8.0 Hz, 1H), 7.44 (m, 1H), 5.43 (m, 1H), 1.48 (d, J = 6.5 Hz, 6H).

PYRIDAZINE DERIVATIVES AS EAAT2 ACTIVATORS

CROSS-REFERENCE TO RELATED APPLICATION

This is a U.S. National Phase Application under 35 U.S.C. 371 of International Patent Application No. PCT/US2012/049311, filed on Aug. 2, 2012, which application claims priority under 35 USC §119(e) to U.S. Provisional Patent Application Ser. No. 61/514,347, filed on Aug. 2, 2011, the entire contents of which are hereby incorporated by reference.

FEDERALLY SPONSORED RESEARCH OR DEVELOPMENT

This invention was made with Government support under Grant Numbers NS049339, NS064275, and NS074601 awarded by the National Institutes of Health. The Government has certain rights in the invention.

TECHNICAL FIELD

This present description relates to pyridazine derivatives that activate the excitatory amino acid transporter 2 (EAAT2), and methods of use thereof for treating or preventing diseases, disorders, and conditions associated with glutamate excitotoxicity.

BACKGROUND

Glutamate is a major neurotransmitter in the mammalian central nervous system (CNS) and essential for normal brain function including cognition, memory, and learning. However, the extracellular concentration of glutamate must remain below excitotoxic levels (~1 uM) to avoid overstimulation of glutamate receptors, leading to neuronal damage or death (Sheldon and Robinson, Neurochem. Int. 2007, 51, 333). Excitotoxicity has been associated with multiple acute neurological conditions such as ischemic stroke, epilepsy, and trauma, chronic adult-onset neurodegenerative disorders such as Alzheimer's disease and amyotrophic lateral sclerosis (ALS) (Guo et al., Hum. Mol. Genet. 2003, 12, 2519; Tian et al., J. Biol. Chem. 2007, 282, 1727; Hazell, Neurochem. Int. 2007 50, 941; Seifert et al., Brain. Res. Rev. 2010, 63, 212; Tian et al., J. Neurochem. 2010, 113, 978), and depression. One potential approach to preventing excitotoxicity is to enhance glutamate reuptake. EAAT2 is the major glutamate transporter and functions to remove glutamate from synapses (Lin et al., Am. J. Physiol. Gastrointest Liver Physiol. 2009, 296, 129). An increase in EAAT2 protein expression and function can provide a means to prevent insufficient glutamate reuptake and consequently reduce neuronal damage.

SUMMARY

The present invention is based, at least in part, on the discovery and development of pyridazine derivatives that activate EAAT2, and are useful in preventing or reducing glutamate excitotoxicity. Thus, described herein are the compounds and methods for their use in treating (e.g., controlling, relieving, ameliorating, alleviating, or slowing the progression of) or preventing (e.g., delaying the onset of or reducing the risk of developing) conditions associated with glutamate excitotoxicity, e.g., acute neurological conditions such as ischemic stroke, epilepsy, and trauma, as well as chronic adult-onset neurodegenerative disorders such as Parkinson's disease, Alzheimer's disease, multiple sclerosis, mesial temporal sclerosis, Huntington's disease, AIDS dementia complex, or amyotrophic lateral sclerosis (ALS); pain disorders including neuropathic pain, visceral pain, or complex regional pain syndrome; addiction including alcohol and cocaine addiction; or cancer, including glioblastoma; and depression.

In some embodiments, the methods described herein can include in vitro methods, e.g., contacting a sample (e.g., a cell or tissue) with a compound of formula (I) or a salt (e.g., a pharmaceutically acceptable salt) thereof as defined anywhere herein.

In some embodiments, the methods can include administering a compound of formula (I) (and/or a compound of any of the other formulae described herein) or a salt (e.g., a pharmaceutically acceptable salt) thereof as defined anywhere herein to a subject (e.g., a subject in need thereof, e.g., a mammal, such as a human).

In one aspect, methods for increasing EAAT2 protein expression in a cell or a subject, e.g., a subject in need thereof, are featured. The methods include administering to the cell or subject an effective amount of a compound of formula (I), or a pharmaceutically acceptable salt thereof:

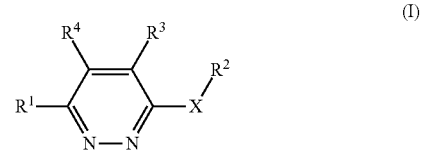

(I)

in which:

$R^1$ is pyridyl or phenyl, each of which is optionally substituted with from 1-5 independently selected $R^a$;

X is S, S(O), SO$_2$, O, NH, N(C$_1$-C$_3$ alkyl), C(O)O, C(O)NH, C(O)NHCH$_2$, C$_1$-C$_4$ alkylene, or a bond;

$R^2$ is:

(i) —Y—$R^5$, wherein Y is C$_1$-C$_8$ alkylene or a bond; and $R^5$ is independently selected from: (a) C$_6$-C$_{10}$ aryl, which is optionally substituted with from 1-5 independently selected $R^b$, (b) heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-5 independently selected $R^b$, (c) C$_1$-C$_8$ alkyl, and (d) H; or (ii) C$_9$-C$_{12}$ aryl-cycloalkyl, wherein the aryl portion is optionally substituted with from 1-5 independently selected $R^b$; or heteroaryl-cycloalkyl, which contains from 9-12 ring atoms, wherein from 1-4 of the ring atoms is independently selected from N, NH, N(C$_1$-C$_3$ alkyl), O, and S; and wherein said heteroaryl portion is optionally substituted with from 1-3 independently selected $R^b$;

each of $R^3$ and $R^4$ is independently selected from hydrogen and C$_1$-C$_3$ alkyl;

$R^a$ at each occurrence is, independently, selected from halo, —OH, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, and —CN; and $R^b$ at each occurrence is independently selected from any of the substituents delineated in (a) (b), (c), (d), (e), and (f), inclusive, below:

(a) halo;
(b) $C_1$-$C_6$ alkyl or $C_1$-$C_6$ haloalkyl, each of which is optionally substituted with —NH($C_1$-$C_6$ alkyl), N($C_1$-$C_6$ alkyl)$_2$, —NHC(O)($C_1$-$C_6$ alkyl);
(c) —OH; $C_1$-$C_6$ alkoxy; $C_{2-8}$ alkynyloxy; $C_1$-$C_6$ haloalkoxy; $C_1$-$C_6$ thioalkoxy; $C_1$-$C_6$ thiohaloalkoxy; —NH$_2$; azido; —NH($C_1$-$C_6$ alkyl), N($C_1$-$C_6$ alkyl)$_2$, —NHC(O)($C_1$-$C_6$ alkyl), wherein the alkyl portion of each is optionally substituted with cyano;
(d) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said cycloalkyl and heterocyclyl is optionally substituted with from 1-3 independently selected $C_1$-$C_4$ alkyl groups;
(e) $C_2$-$C_4$ alkenyl; $C_2$-$C_8$ alkynyl;
(f) nitro; cyano; —C(O)H; —C(O)($C_1$-$C_6$ alkyl); C(O)OH; —C(O)O($C_1$-$C_6$ alkyl); —C(O)NH$_2$—SO$_2$($C_1$-$C_6$ alkyl); —SO$_2$($C_1$-$C_6$ haloalkyl); —C(O)NR'''R''''—SO$_2$NR'''R'''', —SO$_2$NH$_2$, —NHCO($C_1$-$C_6$ alkyl), —NHSO$_2$($C_1$-$C_6$ alkyl), whereby R''' and R'''' is independently selected from H, $C_1$-$C_6$ alkyl, $C_1$-$C_6$ haloalkyl.

In another aspect, compounds of formula (I), or a pharmaceutically acceptable salt thereof, are featured:

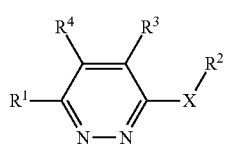

in which:
$R^1$, $R^2$, $R^3$, $R^4$, and X can be as defined anywhere herein.
In some embodiments:
provided that when $R^1$ is 2-pyridyl, X is S, and Y is CH$_2$, then $R^5$ is not 2-chloro-6-fluorophenyl, 2-methylphenyl, 2,5-dimethylphenyl, 2-chlorophenyl, 2-fluorophenyl, 2-chloro-4,6-difluorophenyl, 2,4-dichlorophenyl, 3,4-dichlorophenyl, 3-chlorophenyl, 3-methylphenyl, or phenyl; and
provided that when $R^1$ is 3-pyridyl, X is S, and Y is CH$_2$, then $R^5$ is not 2-chlorophenyl or 2-methylphenyl; and
provided that when $R^1$ is 4-pyridyl, X is S, and Y is CH$_2$, then $R^5$ is not 2-methylphenyl.

In some embodiments, X is S, S(O), SO$_2$; O, NH, N($C_1$-$C_3$ alkyl), or a bond.
In some embodiments, X is $C_1$-$C_4$ alkylene.
In some embodiments, X is —CH$_2$—.
In some embodiments, X is O or S (e.g., S).
In some embodiments, $R^5$ is independently selected from:
(a) $C_6$-$C_{10}$ aryl, which is optionally substituted with from 1-5 independently selected $R^b$, and (b) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-5 independently selected $R^b$, wherein $R^b$ can be as defined anywhere herein.

In one aspect, pharmaceutical compositions are featured, which include a compound of formula (I), or a pharmaceutically acceptable salt thereof (e.g., including any subgenera or specific compound thereof of formula (I)) and a pharmaceutically acceptable carrier.

In one aspect, methods for reducing the extracellular concentration of glutamate (e.g., to a concentration that is below excitotoxic levels, e.g., less than 1 μM) are featured. The methods include contacting a subject (e.g., a subject in need thereof), tissue, or cell with a compound of formula (I), or a pharmaceutically acceptable salt thereof (e.g., including any subgenera or specific compound thereof of formula (I)):

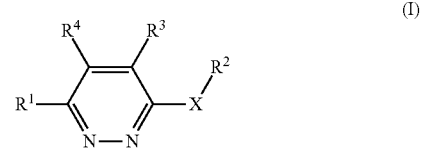

wherein $R^1$, $R^2$, $R^3$, $R^4$, and X can be as defined anywhere herein.

In another aspect, methods for maintaining an extracellular concentration of glutamate that is below excitotoxic levels are featured (e.g., less than 1 μM). The methods include contacting a subject (e.g., a subject in need thereof), tissue, or cell with a compound of formula (I), or a pharmaceutically acceptable salt thereof (e.g., including any subgenera or specific compound thereof of formula (I)):

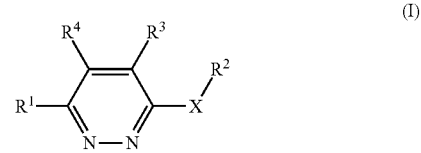

wherein $R^1$, $R^2$, $R^3$, $R^4$, and X can be as defined anywhere herein.

In a further aspect, methods for treating or preventing glutamate excitotoxicity in a subject (e.g., in need thereof) are featured. The methods include administering to the subject an effective amount of a compound of formula (I), or a pharmaceutically acceptable salt thereof (e.g., including any subgenera or specific compound thereof of formula (I)):

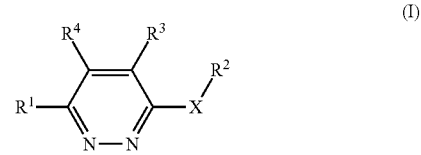

wherein $R^1$, $R^2$, $R^3$, $R^4$, and X can be as defined anywhere herein.

In one aspect, methods for treating or preventing a disease, disorder, or condition associated with glutamate excitotoxicity in a subject in need thereof are featured. The methods include administering to the subject an effective amount of a compound of formula (I), or a pharmaceutically acceptable salt thereof (e.g., including any subgenera or specific compound thereof of formula (I)):

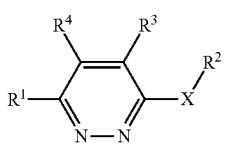

wherein $R^1$, $R^2$, $R^3$, $R^4$, and X can be as defined anywhere herein.

In some embodiments, the disease, disorder, or condition is ischemic stroke, epilepsy, trauma, or a chronic neurodegenerative disorder including Alzheimer's disease, amyotrophic lateral sclerosis (ALS), Huntington's disease, Parkinson's disease, multiple sclerosis or pain disorders including neuropathic pain, visceral pain, complex regional pain syndrome or addiction including alcohol, cocaine or cancer including glioblastoma. In some embodiments, the disease, disorder, or condition is depression.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In another aspect, methods of screening for (thereby identifying) compounds that activate EAAT2 are featured.

In a further aspect, methods of making the compounds described herein are featured. In some embodiments, the methods include taking any one of the intermediate compounds described herein and reacting it with one or more chemical reagents in one or more steps to produce a compound of formula (I) (and/or a compound of any of the other formulae described herein) or a salt (e.g., a pharmaceutically acceptable salt) thereof as defined anywhere herein.

In one aspect, methods of making the pharmaceutical compositions described herein are featured. In some embodiments, the methods include taking any one or more of the compounds of formula (I) (and/or compounds of any of the other formulae described herein) or a salt (e.g., a pharmaceutically acceptable salt) thereof as defined anywhere herein, and mixing said compound(s) with one or more pharmaceutically acceptable carriers.

Embodiments described herein can include any one or more of the following features.

$R^1$ is pyridyl (e.g., 2-pyridyl, 3-pyridyl, 4-pyridyl. In some embodiments, $R^1$ is 2-pyridyl).

X is O or S (e.g., S).

Each of $R^3$ and $R^4$ is hydrogen.

$R^2$ is $-Y-R^5$.

In some embodiments, Y is $C_1$-$C_8$ alkylene (e.g., $C_1$-$C_4$ alkylene, e.g., —$CH_2$— or $C_2$-$C_4$ alkylene, e.g., $C_2$ alkylene, e.g., —$CH_2CH_2$— or —$CH(CH_3)$—; e.g., $C_2$-$C_8$ alkylene, e.g., $C_3$-$C_8$ alkylene, e.g., $C_4$-$C_8$ alkylene, e.g., $C_2$-$C_6$ alkylene, e.g., $C_3$-$C_6$ alkylene).

In some embodiments, $R^5$ is $C_6$-$C_{10}$ aryl (e.g., phenyl), which is optionally substituted with from 1-5 (e.g., 1-3) independently selected $R^b$.

In some embodiments, $R^b$ is $C_1$-$C_6$ alkyl (e.g., $C_1$-$C_3$ alkyl, e.g., $CH_3$); $C_1$-$C_6$ haloalkyl (e.g., $C_1$-$C_3$ haloalkyl, e.g., $CF_3$); halo (e.g., chloro or fluoro); or cyano.

In certain embodiments, $R^b$ is $C_1$-$C_6$ alkyl (e.g., $C_1$-$C_3$ alkyl, e.g., $CH_3$); or halo (e.g., chloro or fluoro).

In certain embodiments, $R^b$ is $C_1$-$C_6$ alkyl (e.g., $C_1$-$C_3$ alkyl, e.g., $CH_3$).

In certain embodiments, $R^b$ is halo (e.g., fluoro or chloro).

In certain embodiments, $R^b$ is azido.

In certain embodiments, $R^b$ is $C_2$-$C_8$ alkynyloxy (e.g., hex-5-yn-1-yloxy).

In certain embodiments, $R^b$ is $C_2$-$C_8$ alkynyl.

In some embodiments, $R^5$ has the following formula:

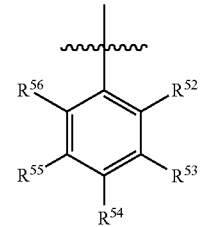

in which 1, 2, or 3 of $R^{52}$, $R^{53}$, $R^{54}$, $R^{55}$, and $R^{56}$ is/are an independently selected $R^b$, and the others are hydrogen, in which $R^b$ can be as defined anywhere herein.

In certain embodiments, one of $R^{52}$ and $R^{56}$ is $R^b$. In embodiments, the other of $R^{52}$ and $R^{56}$ is an independently selected $R^b$ and/or $R^{54}$ is an independently selected $R^b$.

In certain embodiments, each occurrence of $R^b$ is an independently selected $C_1$-$C_6$ alkyl (e.g., $C_1$-$C_3$ alkyl, e.g., $CH_3$). In other embodiments, each occurrence of $R^b$ is independently selected from fluoro and chloro.

In certain embodiments, $R^5$ is: 2-methylphenyl, 2-chlorophenyl, 2,6-dimethylphenyl, 2,4-dimethylphenyl, 2,6-dichlorophenyl, 2-fluorophenyl, 2,4-difluorophenyl, 3-chlorophenyl, 2,4,6-trimethylphenyl, 2-chloro-6-fluorophenyl, 2,3-dichlorophenyl, 2,4-dichlorophenyl, 2,5-dichlorophenyl, 2,6-difluorophenyl, 2,4,6-trifluorophenyl, 4-fluorophenyl, 2-chloro-4-fluorophenyl, 3-methylphenyl, or 4-methylphenyl. For example, $R^5$ can be 2-methylphenyl, 2-chlorophenyl, 2,6-dimethylphenyl, 2,4-dimethylphenyl, 2,6-dichlorophenyl, 2-fluorophenyl, 2,4-difluorophenyl, 3-chlorophenyl, 2,4,6-trimethylphenyl, 2-chloro-6-fluorophenyl, or 2-azido-4-(hex-5-yn-1-yloxy)phenyl.

In some embodiments, $R^2$ is $C_9$-$C_{12}$ aryl-cycloalkyl, wherein the aryl portion is optionally substituted with from 1-5 independently selected $R^b$; or heteroaryl-cycloalkyl, which contains from 9-12 ring atoms, wherein from 1-4 of the ring atoms is independently selected from N, NH, N($C_1$-$C_3$ alkyl), O, and S; and wherein said heteroaryl portion is optionally substituted with from 1-3 independently selected $R^b$. In certain embodiments, $R^2$ is $C_9$-$C_{12}$ aryl-cycloalkyl, wherein the aryl portion is optionally substituted with from 1-5 independently selected $R^b$ (e.g., tetrahydronaphthyl).

In some embodiments, the compound of formula (I) is selected from the compounds as shown in FIG. 1.

In some embodiments:

$R^1$ is pyridyl (e.g., 2-pyridyl, 3-pyridyl, or 3-pyridyl. In some embodiments, R1 is 2-pyridyl); and X is O or S (e.g., S); and each of $R^3$ and $R^4$ is hydrogen;

$R^2$ is $-Y-R^5$, in which Y and $R^5$ can be as defined anywhere herein. For example:

Y is $C_1$-$C_8$ alkylene (e.g., $C_1$-$C_4$ alkylene, e.g., —$CH_2$— or $C_2$-$C_4$ alkylene, e.g., $C_2$ alkylene, e.g., —$CH_2CH_2$— or —CH(CH$_3$)—; e.g., C$_2$-C$_8$ alkylene, e.g., C$_3$-C$_8$ alkylene, e.g., C$_4$-C$_8$ alkylene, e.g., C$_2$-C$_6$ alkylene, e.g., C$_3$-C$_6$ alkylene); and R$^5$ is C$_6$-C$_{10}$ aryl (e.g., phenyl), which is optionally substituted with from 1-5 (e.g., 1-3) independently selected R$^b$, in which R$^b$ can be as defined anywhere herein.

In some embodiments:
provided that when R$^1$ is 2-pyridyl, X is S, and Y is CH$_2$, then R$^5$ is not 2-chloro-6-fluorophenyl, 2-methylphenyl, 2,5-dimethylphenyl, 2-chlorophenyl, 2-fluorophenyl, 2-chloro-4,6-difluorophenyl, 2,4-dichlorophenyl, 3,4-dichlorophenyl, 3-chlorophenyl, 3-methylphenyl, or phenyl; and
provided that when R$^1$ is 3-pyridyl, X is S, and Y is CH$_2$, then R$^5$ is not 2-chlorophenyl or 2-methylphenyl; and
provided that when R$^1$ is 4-pyridyl, X is S, and Y is CH$_2$, then R$^5$ is not 2-methylphenyl.

In some embodiments, any compound, composition, or method described herein can also include any one or more of the other features delineated in the detailed description and/or in the claims.

The term "mammal" includes organisms, which include mice, rats, cows, sheep, pigs, rabbits, goats, horses, monkeys, dogs, cats, and humans.

In embodiments, an amount of a compound of formula (I) or salt thereof can be an effective amount. "An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect can be objective (i.e., measurable by some test or marker) or subjective (i.e., subject gives an indication of or feels an effect). An effective amount of the compound described above can range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (Here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, and polycyclic rings.

The following definitions are used unless otherwise described. Specific and general values listed below for radicals, substituents, and ranges are for illustration only. They do not exclude other defined values or other values within defined ranges for the radicals and substituents. Unless otherwise indicated, alkyl, alkylene, alkoxy, alkenyl, and the like denote both straight and branched groups.

The term "alkyl" refers to a saturated hydrocarbon chain that can be a straight chain or branched chain, containing the indicated number of carbon atoms. For example, C$_1$-C$_6$ alkyl indicates that the group can have from 1 to 6 (inclusive) carbon atoms in it. Any atom can be optionally substituted, e.g., by one or more substituents. Examples of alkyl groups include, without limitation, methyl, ethyl, n-propyl, isopropyl, and tert-butyl.

As used herein, the term "C$_{n-m}$ alkylene," employed alone or in combination with other terms, refers to a non-branched divalent alkyl linking group having n to m carbon atoms. Alkylene groups typically connect two other different groups (e.g., Y in formula (I) can be an alkylene that connects variables X and R$^5$). In some embodiments, for alkylenes having two or more carbon atoms, two different carbon atoms can each serve as a point of attachment (e.g., X—CH$_2$CH$_2$—R$^5$, i.e., in which Y is 1,2-diethylene). In other embodiments, for alkylenes having two or more carbon atoms, the same carbon atom can serve as the point of attachment (e.g., X—C(H)(CH$_3$)—R$^5$, i.e., in which Y is 1,1-diethylene). Other examples of alkylene include methylene (i.e., —CH$_2$—).

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) is replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, tert-butoxy, pentoxy, 2-pentoxy, 3-pentoxy, or hexyloxy. Likewise, the term "thioalkoxy" refers to a group of formula —S(alkyl). The terms "haloalkoxy" and "thio-haloalkoxy" refer to —O(haloalkyl) and —S(haloalkyl), respectively. Finally, the term "heterocyclyloxy" refers to a group of the formula —O(heterocyclyl).

The term "alkynyloxy" refers to a group of formula —O(alkynyl). Alkynyloxy can be, for example, penta-4-yn-1-yloxy, hex-5-yn-1-yloxy, hept-6-yn-1-yloxy, penta-3-yn-1-yloxy, hex-3-yn-1-yloxy, hept-4-yn-1-yl-oxy.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include groups such as ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups can be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include groups such as tetrahydrofuryl, tetrahydropyranyl, piperidyl (piperidino), piperazinyl, morpholinyl (morpholino), pyrrolinyl, and pyrrolidinyl. By way of example, a phrase such as "heterocyclic ring containing from 5-6 ring atoms", wherein from 1-2 of the ring atoms is independently selected from N, NH, N($C_1$-$C_6$ alkyl), NC(O) ($C_1$-$C_6$ alkyl), O, and S; and wherein said heterocyclic ring is optionally substituted with from 1-3 independently selected $R^a$ would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon group. Any atom can be optionally substituted, e.g., by one or more substituents. A ring carbon serves as the point of attachment of a cycloalkyl group to another moiety. Cycloalkyl moieties can include groups such as cyclopropyl, cyclobutyl, cyclopentyl, cyclohexyl, cycloheptyl, adamantyl, and norbornyl (bicyclo[2.2.1]heptyl).

The term "aryl" refers to an aromatic monocyclic, bicyclic (2 fused rings), tricyclic (3 fused rings), or polycyclic (>3 fused rings) hydrocarbon ring system. One or more ring atoms can be optionally substituted by one or more substituents for example. Aryl moieties include groups such as phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups can be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The term "aryl-cycloalkyl" refers to bicyclic or tricyclic ring systems that include an aryl ring fused to a cycloalkyl. Any atom can be substituted, e.g., by one or more substituents. For example, arylcycloalkyl can include indanyl or tetrahydronaphthyl. Either the aryl or cycloalkyl (e.g., cycloalkyl) portion can serve as the point of attachment to another moiety.

The term "heteroaryl-cycloalkyl" refers to bicyclic or tricyclic ring systems that include a heteroaryl ring fused to a cycloalkyl. Any atom can be substituted, e.g., by one or more substituents. Either the heteroaryl or cycloalkyl (e.g., cycloalkyl) portion can serve as the point of attachment to another moiety.

As used herein, the descriptor "—CN" represents the cyano group (and vice versa), wherein the carbon and nitrogen atoms are bound together by a triple bond. As used herein, the descriptor "—OH" represents the hydroxy group (and vice versa). The descriptors "C=O" or "C(O)" refers to a carbon atom that is doubly bonded to an oxygen atom.

In general, when a definition for a particular variable includes hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on groups such as an alkyl, haloalkyl, cycloakyl, heterocyclyl, aryl, or heteroaryl group at any atom of that group. In one aspect, the substituent(s) on a group are independently any one single or any combination of two or more of the permissible atoms or groups of atoms delineated for that substituent. In another aspect, a substituent can itself be substituted with any one of the above substituents.

Further, as used herein, the phrase "optionally substituted" means unsubstituted (e.g., substituted with hydrogen (H)) or substituted. As used herein, the term "substituted" means that a hydrogen atom is removed and replaced by a substituent. It is understood that substitution at a given atom is limited by valency.

Descriptors such as "$C_6$-$C_{10}$ aryl that is optionally substituted with from 1-4 independently selected $R^b$ (and the like) is intended to include both an unsubstituted $C_6$-$C_{10}$ aryl group and a $C_6$-$C_{10}$ aryl group that is substituted with from 1-4 independently selected $R^b$. The use of a substituent (radical) prefix name such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

Dosage

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
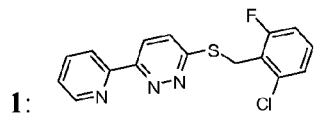
FIG. 1 shows structures of exemplary compounds described herein and analytical data for the compounds.
Figure 1:
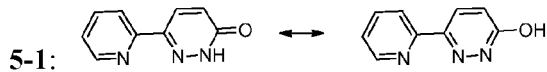
Figure 1:
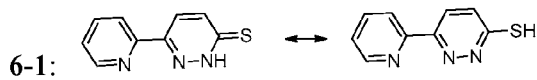
Figure 1:
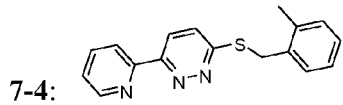
Figure 1:
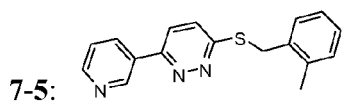
Figure 1:
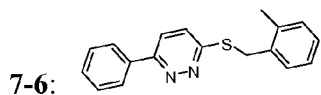
Figure 1:
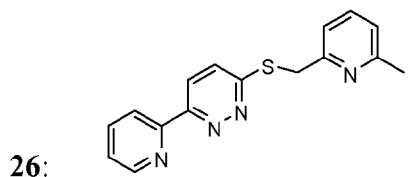
Figure 1:
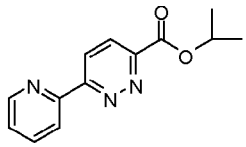

The pyridazine derivatives described herein activate EAAT2, and thus are useful in methods of reducing extracellular glutamate levels, thereby reducing glutamate excitotoxicity in cells and tissues, making them therapeutically useful in treating or preventing conditions associated with glutamate excitotoxicity, e.g., acute neurological conditions such as ischemic stroke, epilepsy, and trauma, as well as chronic adult-onset neurodegenerative disorders such as Alzheimer's disease and amyotrophic lateral sclerosis (ALS). In some embodiments, the pyridazine derivatives described herein are therapeutically useful in treating or preventing depression.

Pyridazine Derivatives

Embodiments can include any one or more of the following features.

$R^1$ is pyridyl (e.g., 2-pyridyl, 3-pyridyl, or 4-pyridyl. In some embodiments, R1 is 2-pyridyl).

X is O or S (e.g., S).

Each of $R^3$ and $R^4$ is hydrogen.

$R^2$ is —Y—$R^5$.

In some embodiments, Y is $C_1$-$C_8$ alkylene (e.g., $C_1$-$C_4$ alkylene, e.g., —$CH_2$— or $C_2$-$C_4$ alkylene, e.g., $C_2$ alkylene, e.g., —$CH_2CH_2$— or —$CH(CH_3)$—; e.g., $C_2$-$C_8$ alkylene, e.g., $C_3$-$C_8$ alkylene, e.g., $C_4$-$C_8$ alkylene, e.g., $C_2$-$C_6$ alkylene, e.g., $C_3$-$C_6$ alkylene).

In some embodiments, $R^5$ is $C_6$-$C_{10}$ aryl (e.g., phenyl), which is optionally substituted with from 1-5 (e.g., 1-3) independently selected $R^b$.

In some embodiments, $R^b$ is $C_1$-$C_6$ alkyl (e.g., $C_1$-$C_3$ alkyl, e.g., $CH_3$); $C_1$-$C_6$ haloalkyl (e.g., $C_1$-$C_3$ haloalkyl, e.g., $CF_3$); halo (e.g., chloro or fluoro); or cyano.

In certain embodiments, $R^b$ is $C_1$-$C_6$ alkyl (e.g., $C_1$-$C_3$ alkyl, e.g., $CH_3$); or halo (e.g., chloro or fluoro).

In certain embodiments, $R^b$ is $C_1$-$C_6$ alkyl (e.g., $C_1$-$C_3$ alkyl, e.g., $CH_3$).

In certain embodiments, $R^b$ is halo (e.g., fluoro or chloro).

In certain embodiments, $R^b$ is azido.

In certain embodiments, $R^b$ is $C_2$-$C_8$ alkynyloxy (e.g., 5-hexynyl-1-oxy).

In certain embodiments, $R^b$ is $C_2$-$C_8$ alkynyl.

In some embodiments, $R^5$ has the following formula:

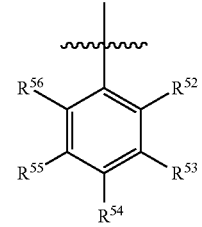

in which 1, 2, or 3 of $R^{52}$, $R^{53}$, $R^{54}$, $R^{55}$, and $R^{56}$ is/are an independently selected $R^b$, and the others are hydrogen, in which $R^b$ can be as defined anywhere herein.

In certain embodiments, one of $R^{52}$ and $R^{56}$ is $R^b$. In embodiments, the other of $R^{52}$ and $R^{56}$ is an independently selected $R^b$ and/or $R^{54}$ is an independently selected $R^b$.

In certain embodiments, each occurrence of $R^b$ is an independently selected $C_1$-$C_6$ alkyl (e.g., $C_1$-$C_3$ alkyl, e.g., $CH_3$). In other embodiments, each occurrence of $R^b$ is independently selected from fluoro and chloro.

In certain embodiments, $R^5$ is: 2-methylphenyl, 2-chlorophenyl, 2,6-dimethylphenyl, 2,4-dimethylphenyl, 2,6-dichlorophenyl, 2-fluorophenyl, 2,4-difluorophenyl, 3-chlorophenyl, 2,4,6-trimethylphenyl, 2-chloro-6-fluorophenyl, 2,3-dichlorophenyl, 2,4-dichlorophenyl, 2,5-dichlorophenyl, 2,6-difluorophenyl, 2,4,6-trifluorophenyl, 4-fluorophenyl, 2-chloro-4-fluorophenyl, 3-methylphenyl, or 4-methylphenyl. For example, $R^5$ can be 2-methylphenyl, 2-chlorophenyl, 2,6-dimethylphenyl, 2,4-dimethylphenyl, 2,6-dichlorophenyl, 2-fluorophenyl, 2,4-difluorophenyl, 3-chlorophenyl, 2,4,6-trimethylphenyl, 2-chloro-6-fluorophenyl), or 2-azido-4-(hex-5-yn-1-yloxy)phenyl.

In some embodiments, $R^2$ is $C_9$-$C_{12}$ aryl-cycloalkyl, wherein the aryl portion is optionally substituted with from 1-5 independently selected $R^b$; or heteroaryl-cycloalkyl, which contains from 9-12 ring atoms, wherein from 1-4 of the ring atoms is independently selected from N, NH, N($C_1$-$C_3$ alkyl), O, and S; and wherein said heteroaryl portion is optionally substituted with from 1-3 independently selected $R^b$. In certain embodiments, $R^2$ is $C_9$-$C_{12}$ aryl-cycloalkyl, wherein the aryl portion is optionally substituted with from 1-5 independently selected $R^b$ (e.g., tetrahydronaphthyl).

In some embodiments, the compound of formula (I) is selected from the compounds as shown in FIG. 1.

In some embodiments:
  $R^1$ is pyridyl (e.g., 2-pyridyl, 3-pyridyl, or 4-pyridyl. In some embodiments, R1 is 2-pyridyl); and
  X is O or S (e.g., S); and
  each of $R^3$ and $R^4$ is hydrogen;
  $R^2$ is —Y—$R^5$, in which Y and $R^5$ can be as defined anywhere herein. For example:
    Y is $C_1$-$C_8$ alkylene (e.g., $C_1$-$C_4$ alkylene, e.g., —$CH_2$— or $C_2$-$C_4$ alkylene, e.g., $C_2$ alkylene, e.g., —$CH_2CH_2$— or —$CH(CH_3)$—; e.g., $C_2$-$C_8$ alkylene, e.g., $C_3$-$C_8$ alkylene, e.g., $C_4$-$C_8$ alkylene, e.g., $C_2$-$C_6$ alkylene, e.g., $C_3$-$C_6$ alkylene); and
    $R^5$ is $C_6$-$C_{10}$ aryl (e.g., phenyl), which is optionally substituted with from 1-5 (e.g., 1-3) independently selected $R^b$, in which $R^b$ can be as defined anywhere herein.

In some embodiments:
  provided that when $R^1$ is 2-pyridyl, X is S, and Y is $CH_2$, then $R^5$ is not 2-chloro-6-fluorophenyl, 2-methylphenyl, 2,5-dimethylphenyl, 2-chlorophenyl, 2-fluorophenyl, 2-chloro-4,6-difluorophenyl, 2,4-dichlorophenyl, 3,4-dichlorophenyl, 3-chlorophenyl, 3-methylphenyl, or phenyl; and
  provided that when $R^1$ is 3-pyridyl, X is S, and Y is $CH_2$, then $R^5$ is not 2-chlorophenyl or 2-methylphenyl; and
  provided that when $R^1$ is 4-pyridyl, X is S, and Y is $CH_2$, then $R^5$ is not 2-methylphenyl.

Compound Forms and Salts

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. The compounds described herein can also be represented in multiple tautomeric forms; in such instances, the present description expressly includes all tautomeric forms of the compounds described herein, even though only a single tautomeric form can be represented. All such isomeric forms of such compounds are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds described herein include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds described herein include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydro iodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products can be obtained by such quaternization. Salt forms of the compounds of any of the formulae herein can be amino acid salts of carboxy groups (e.g. L-arginine, -lysine, -histidine salts).

Lists of suitable salts are found in *Remington's Pharmaceutical Sciences*, 17th ed., Mack Publishing Company, Easton, Pa., 1985, p. 1418; Journal of Pharmaceutical Science, 66, 2 (1977); *"Pharmaceutical Salts: Properties, Selection, and Use A Handbook*; Wermuth, C. G. and Stahl, P. H. (eds.) Verlag Helvetica Chimica Acta, Zurich, 2002; and Berge et al. (1977) "Pharmaceutical Salts", J. Pharm. Sci. 66:1-19; each of which is incorporated herein by reference in its entirety.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the present description provides compounds which are in a prodrug form. Prodrugs of the compounds described herein are those compounds that undergo chemical changes under physiological conditions to provide the compounds described herein. Additionally, prodrugs can be converted to the compounds described herein by chemical or biochemical methods in an ex vivo environment. For example, prodrugs can be slowly converted to the compounds described herein when placed in a transdermal patch reservoir with a suitable enzyme or chemical reagent. Prodrugs are often useful because, in some situations, they can be easier to administer than the parent drug. They can, for instance, be more bioavailable by oral administration than the parent drug. The prodrug can also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound described herein which is administered as an ester (the "prodrug"), but then is metabolically hydrolyzed to the carboxylic acid, the active entity. In embodiments, the ester can be an alkyl ester (e.g., $C_1$-$C_3$ alkyl, e.g., $CH_3$ or $CH_2CH_3$; or $C_3$-$C_6$ alkyl, e.g., $C_3$-$C_6$ branched alkyl, e.g., t-butyl, isopropyl, isobutyl). Additional examples include peptidyl derivatives of a compound described herein.

Also included herein are various hydrate and solvate forms of the compounds (and salts thereof) described herein.

The compounds described herein can also contain unnatural proportions of atomic isotopes at one or more of the atoms that constitute such compounds. For example, the compounds can be radiolabeled with radioactive isotopes, such as for example tritium ($^3H$), iodine-125 ($^{125}I$) or carbon-14 ($^{14}C$). All isotopic variations of the compounds described herein whether radioactive or not, are intended to be encompassed within the scope of the invention.

Synthesis of Compounds

The compounds described herein can be conveniently prepared in accordance with methods known in the art or the procedures outlined in the Examples section, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvents used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy (FT-IR), spectrophotometry (e.g., UV-visible), or mass spectrometry (MS), or by chromatography such as high performance liquid chromatograpy (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of solvents. Depending on the particular reaction step, suitable solvents for a particular reaction step can be selected.

The compounds described herein can be prepared, for example, using the reaction pathways and techniques as described below in the Examples.

Pharmaceutical Compositions and Methods of Administration

The methods described herein include the manufacture and use of pharmaceutical compositions, which include compounds described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration.

Examples of routes of administration include parenteral, e.g., intravenous, intradermal, subcutaneous, oral, nasal or intranasal (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

In some embodiments, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Treatment

The methods described herein include methods for the treatment of disorders associated with glutamate excitotoxicity. A number of such disorders are known in the art, and can be readily identified by one of skill in the art. In some embodiments, the disorder is an acute neurological condition such as ischemic stroke, epilepsy, hypoglycemia, hypoxia, or trauma. In some embodiments, the disorder is a chronic neurodegenerative disorder such as Parkinson's disease, Alzheimer's disease, multiple sclerosis, mesial temporal sclerosis, Huntington's disease, AIDS dementia complex, or amyotrophic lateral sclerosis (ALS) (see, e.g., Hu et al., "Glutamate receptors in preclinical research on Alzheimer's disease: Update on recent advances." Pharmacol Biochem Behay. 2011 Apr. 22 [Epub ahead of print, doi: 10.1016/j.pbb.2011.04.013]; Wang and Qin, Apoptosis. 15(11):1382-402 (2010); Kaul and Lipton, Curr HIV Res. 4(3):307-18 (2006); Kim et al., J Cell Physiol. 226(10): 2484-93 (2011); Sheldon and Robinson, Neurochem Int. 51(6-7):333-55 (2007); Guo et al., Hum. Mol. Genet. 2003, 12, 2519; Tian et al., J. Biol. Chem. 282:1727 (2007); Hazell, Neurochem. Int. 50:941 (2007); Seifert et al., Brain. Res. Rev. 63:212 (2010); Tian et al., J. Neurochem. 113:978 (2010); Olney, "Neurotoxicity of excitatory amino acids." In: McGeer E, Olney J, McGeer P, eds. *Kainic Acid as a Tool in Neurobiology*. New York: Raven Press; 1978:95-121; Olney, APMIS Suppl 40:103-112 (2010)). In some embodiments, the disorder is depression (see, e.g., Chen et al., Presynaptic glutamatergic dysfunction in bipolar disorder, Biol. Pshychiatry, 67(11): 1007-1009 (2010)). In some embodiments, glutamate excitotoxicity can be a result of an environmental toxin, e.g., Tributyltin (Nakatsu et al., Toxicol. Sci. (January 2006) 89 (1): 235-242), lead, and domoic acid.

In some embodiments, excessive glutamate is associated with chronic pain disorders including migraine, fibromyalgia, temporomandibular disorders, neuropathic pain, visceral pain, or complex regional pain syndrome; see, e.g., Chizh et al., Amino Acids, 23(1-3):169-76 (2002); Descalzi et al., Mol Neurobiol. 40(3):253-9. Epub 2009 Oct. 11 (2009); Larsson, Mol Neurobiol. 40(3):260-88 (2009); Yogeswaari et al., Expert Opin Ther Targets. 13(8):925-43 (2009); Vargas, Curr Pain Headache Rep. 13(1):64-6 (2009).

Disruptions in glutamate homeostasis are associated with addictive disorders. As substance abuse develops into addiction, neurochemistry shifts from dopamine-based to predominantly glutamate-based. Thus, subjects suffering from drug addiction and dependence, including alcohol and cocaine addiction, can also be treated using the methods described herein. See, e.g., Tzschentke, Amino Acids 23(1-3):147-52 (2002); Reissner and Kalivas, Behav Pharmacol. 2010 September; 21(5-6):514-22 (2010); and Myers et al., Neuropsychopharmacology. 36(1):274-93 (2011).

Glutamate has also been shown to play a role in some cancers, including necrosis in glioblastoma, which is associated with poor prognosis. See, e.g., Noch and Khalili, Cancer Biol Ther. 8(19):1791-7 (2009). Thus, the methods and compositions described herein can be used to treat subjects with cancers, e.g., brain cancers such as glioblastoma. Glutamate has been shown to play a role in modulating various mood disorders, for example, major depressive disorder (Owen, Drugs today, 2012, 48(7):469-78)).

Generally, the methods include administering a therapeutically effective amount of a pyridazine derivative as described herein, to a subject who is in need of, or who has been determined to be in need of, such treatment.

The presence of a disorder associated with glutamate excitotoxicity can be diagnosed or determined using methods known in the art, including spectroscopy at 0.5 T to observe the combined glutamate and glutamine (glx) peak (see, e.g., Prost et al., Magn Reson Med 1997; 37:615-618; Mark et al., American Journal of Neuroradiology 22:1813-1824 (2001)). Other known clinical diagnostic methods can also be used to diagnose the presence of a disorder known to be associated with glutamate excitotoxicity, e.g., as described herein.

In some embodiments, glutamate excitotoxicity (and subsequent neurological damage) can be a result of an environmental toxin, e.g., Tributyltin (Nakatsu et al., Toxicol. Sci. (January 2006) 89 (1): 235-242), lead, and domoic acid. Subjects who have been or will be exposed to such toxins can be considered to have a disorder associated with glutamate excitotoxicity and can be treated using the methods described herein. In some embodiments subjects who have been exposed to an environmental toxin known to cause or contribute to glutamate excitotoxicity can be treated using the methods described herein before the onset of clinical (e.g., neurological) symptoms, to prevent or reduce the risk of a disorder associated with glutamate excitotoxicity.

As used in this context, to "treat" means to ameliorate at least one symptom of the disorder associated with glutamate excitotoxicity. Often, glutamate excitotoxicity results in neuronal cell death; thus, a treatment can result in a reduction in the rate or amount of neuronal cell death.

EXAMPLES

The invention is further described in the following examples, which do not limit the scope of the invention described in the claims.

Example 1

Structure-Activity Relationship Study of Pyridazine Derivatives as Glutamate Transporter EAAT2 Activators In an effort to identify small molecules that can increase EAAT2 protein expression, a high-throughput screen of approximately 140,000 compounds was previously conducted using a cell-based enzyme-linked immunosorbent assay (Colton et al., J. Biomol. Screen. 2010, 15, 653). The hits identified from this screening provide starting points for further optimization in order to arrive at pharmacologically useful molecules for therapeutic agents to treat neuronal injury.

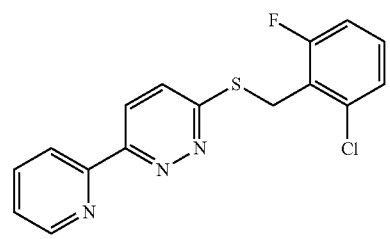

1

The thiopyridazine 1 was confirmed to show a dose-dependent increase in EAAT2 protein levels after 24 h exposure. Described herein is a structure-activity relationship (SAR) study of 1 for elevating EAAT2 protein levels.

Many of the pyridazine analogues utilized in the SAR study were prepared using the method depicted in Scheme 1. Treatment of ketone 2 with glyoxylic acid (3) and $K_2CO_3$ gave 4, which was used directly without purification. It was allowed to react with hydrazine in acetic acid at 100° C. to yield the desired pyridazinone 5 as an off-white solid after recrystallization from ethyl acetate (Coates and McKillop, Synthesis, 1992, 334-342). Direct alkylation of 5 gave 8 in good yields. Intermediate 5 was also converted into pyridazinethione 6 in the presence of $P_2S_5$ in pyridine at 120° C. (Arakawa et al., Chem. Pharm. Bull. 1977, 25, 299). Alkylation of 6 provided 7, which could be further oxidized to sulfone 9 with 3-chloroperoxybenzoic acid (m-CPBA) in $CH_2Cl_2$ (Mylari et al., J. Med. Chem. 2005, 48, 6326).

Scheme 1.

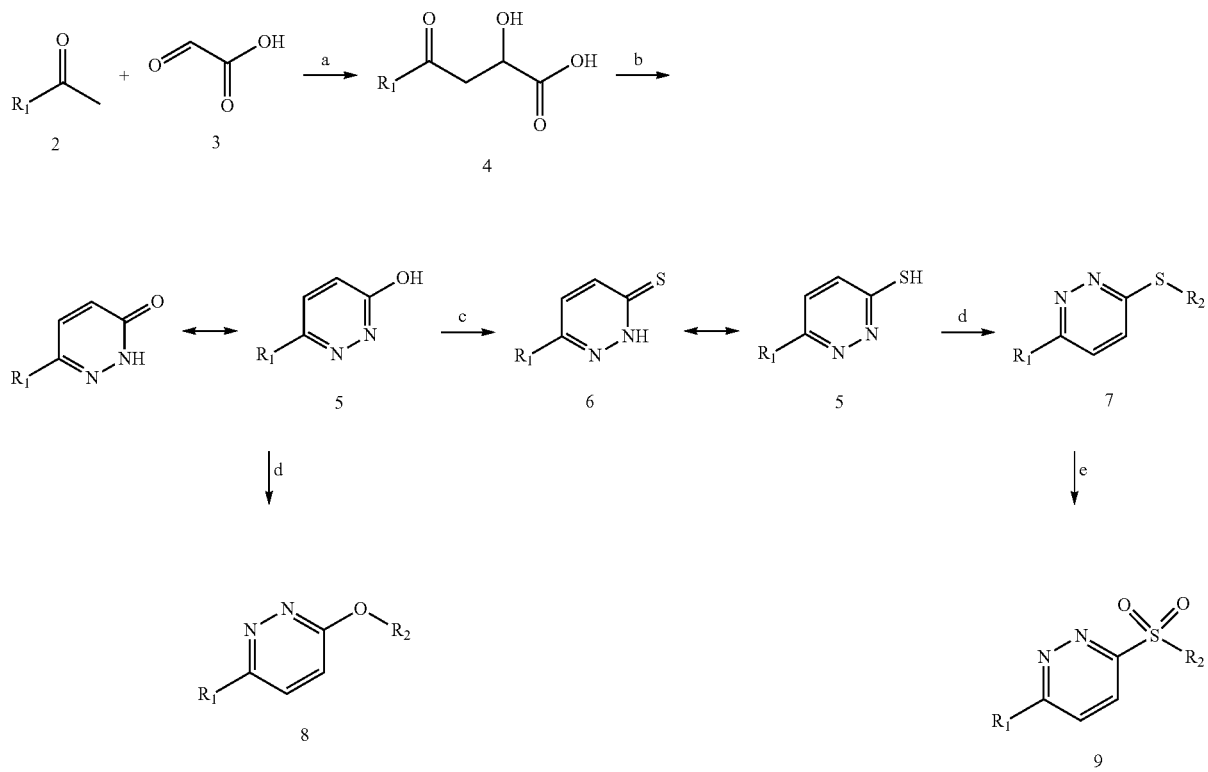

Reagents and conditions:
(a) $K_2CO_3$, $H_2O$;
(b) $NH_2NH_2$, AcOH, 100° C. (20%);
(c) $P_2S_5$, pyridine, 120° C. (80%);
(d) $R^2Br$, $K_2CO_3$, DMF, (90%);
(e) MCPBA, $CH_2Cl_2$ (80%).

A series of additional analogues 14-17 was prepared using the methodology outlined in Scheme 2. Recently, 2-pyridyl N-methyliminodiacetic acid (MIDA) boronate (10) has been reported as an air-stable slow-release reagent with high cross-coupling efficiency even with heteroaryl chlorides (Knapp et al., J. Am. Chem. Soc. 2009, 131, 6961). Therefore, this material was used in palladium-mediated cross-couple reactions with heteroaryl chlorides 11-13 to obtain 14-16, respectively. The ester 16 was then allowed to react with alkylamines in ethanol at 85° C. to generate amides 17.

Scheme 2.

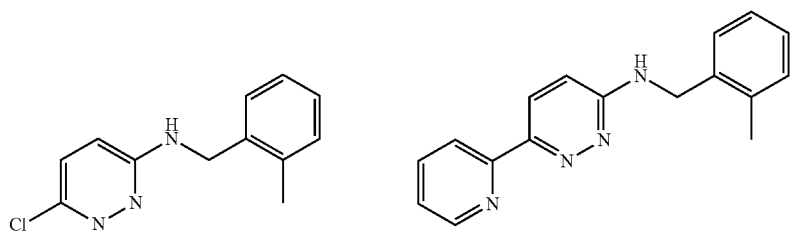

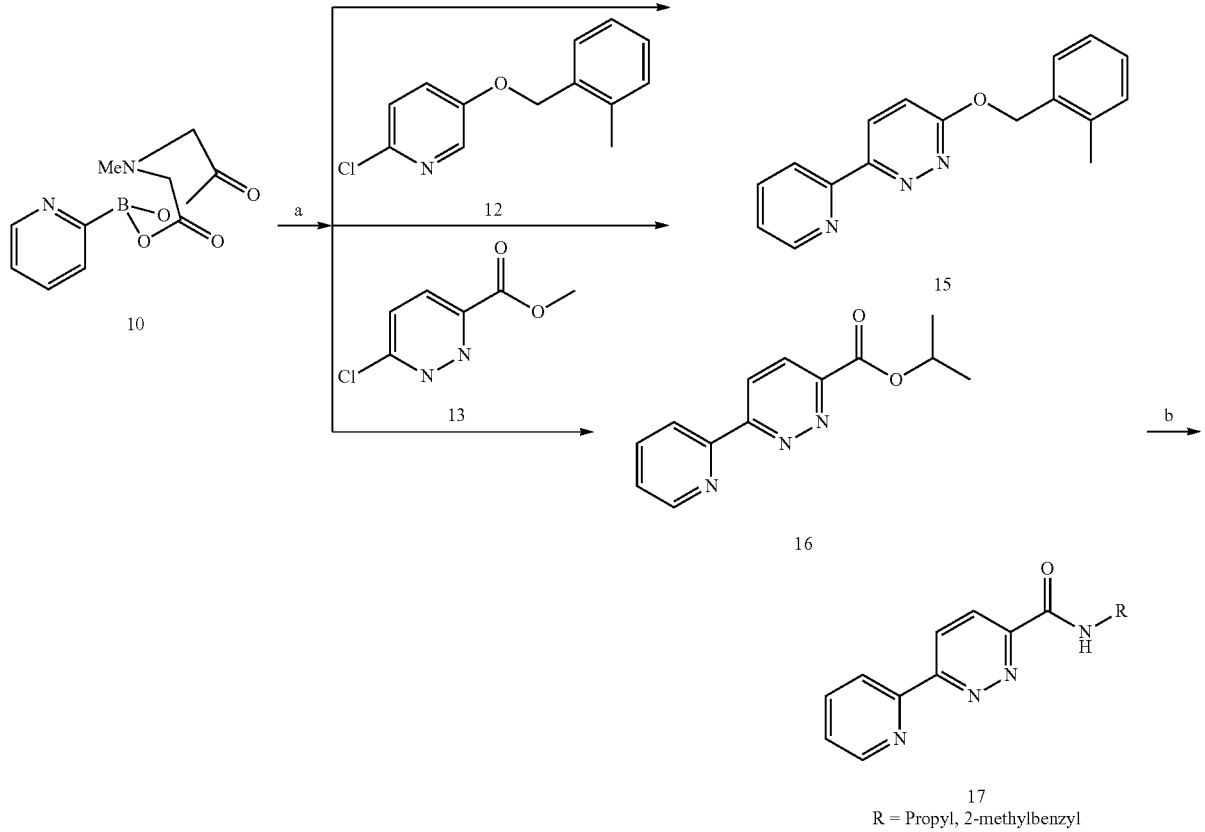

Reagents and conditions:
(a) Pd₂(dba)₃, XPhos, Cu(OAc)₂, K₂CO₃, DMF/IPA (4/1), 100° C.;
(b) H₂NR, ethanol, 85° C. (90%).

Finally, several additional analogues designed to evaluate replacement of the pyridazine in 1 with phenyl and pyridyl moieties, were prepared using the methodology outlined in Scheme 3. Suzuki coupling of 2-bromopyridine (18) with various boronic acids afforded 19 and 20 (Ghiron et al., J. Med. Chem. 2010, 53, 4379). Treatment of 20 with P₂S₅ in pyridine at 120° C. provided 21 in 71% yield. Alkylation of 21 with 2-methylbenzyl bromide in the presence of K₂CO₃ in DMF generated 22.

Scheme 3.

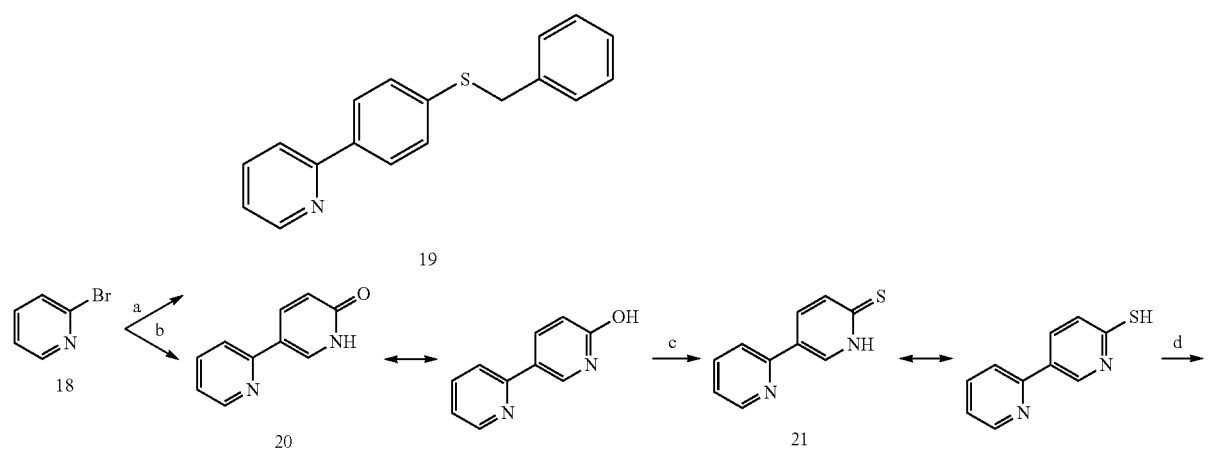

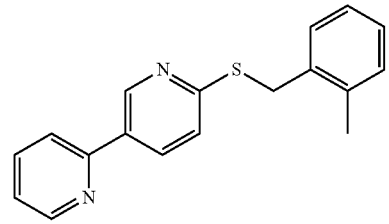

22

Reagents and conditions:
(a) Pd(PPh3)4, Na2CO3, CH3CN/H2O (1/1), 75° C., 4-benzylthiophenylboronic acid (54%);
(b) Pd(PPh3)4, NaCO3, CH3CN/H2O (1/1), 75° C., 6-hydroxypyridine-3-boronic acid pinacol ester (70%);
(c) P2S5, pyridine, 120° C. (71%);
(d) 2-methylbenzyl bromide, K2CO3, DMF (76%).

All of the derivates of 1 were initially evaluated in PA-EAAT2 cells[3] (a primary astrocyte line stably expressing EAAT2 mRNAs) following compound (10 μM) incubation for 4 and 24 h before harvesting and measuring EAAT2 levels by Western blot analysis. The fold increases in EAAT2 protein levels relative to DMSO controls are reported (Tables 1-4).

Replacement of the 2-pyridyl with 3-pyridyl (7-1, 7-5 and 7-8), 4-pyridyl (7-2, 7-9 and 7-11) or phenyl (7-6) resulted in reduced activity (Table 1). Removing either one or both of the nitrogen atoms in the pyridazine resulted in loss of activity (Table 2). Collectively, these results suggested that both the 2-pyridyl and the pyridazine were required for enhancing EAAT2 protein expression.

Activities for compounds 23-27 were also assessed. Compounds 23 and 25-27 were active, while compound 24 was not. For example, compounds 25-26 have respectively 4.2 and 6.5-fold EAAT2 increase at 10 μM (24 h), and compound 27 had a reduced activity of 1.9 fold or less EAAT2 increase at 10 μM (24 h).

TABLE 1

Effects of the modified pyridyl and benzyl substituent on EAAT2 protein levels

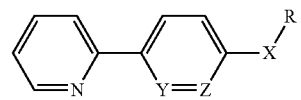

| | | | Fold increase for EAAT2[a] | |
|---|---|---|---|---|
| Compound | R[1] | R[2] | 4 h | 24 h |
| 1 | 2-Py | 2-Cl-6-F—Bn | na[b] | 2.0 ± 0.8 |
| 7-1 | 3-Py | 2-Cl-6-F—Bn | na | 2.3 ± 0.8 |
| 7-2 | 4-Py | 2-Cl-6-F—Bn | na | 1.9 ± 0.9 |
| 7-3 | 4-Me—Ph | 2-Cl-6-F—Bn | 1.2 ± 0.2 | 2.3 ± 0.7 |
| 7-4 | 2-Py | 2-Me—Bn | 1.7 ± 0.1 | 3.5 ± 0.3 |
| 7-5 | 3-Py | 2-Me—Bn | 1.5 ± 0.4 | na |
| 7-6 | Ph | 2-Me—Bn | 1.1 ± 0.1 | 2.0 ± 0.4 |
| 7-7 | 2-Py | 2-Cl—Bn | 2.1 ± 1.4 | 4.0 ± 0.3 |
| 7-8 | 3-Py | 2-Cl—Bn | 1.2 ± 0.4 | 1.2 ± 0.3 |
| 7-9 | 4-Py | 2-Cl—Bn | 1.5 ± 0.2 | 1.7 ± 0.3 |
| 7-10 | 2-Py | 4-Me—Bn | 2.1 ± 1.1 | 2.6 ± 0.4 |
| 7-11 | 4-Py | 4-Me—Bn | 1.3 ± 0.1 | 2.4 ± 0.6 |
| 25 | 4-Me—Py | 2-Me—Bn | na | 4.2 |

[a]Compound concentration of 10 μM;
[b]na = not active

TABLE 2

Effects of modifications of the pyridazine on EAAT2 protein levels

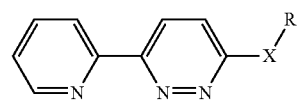

| | | | | | Fold increase for EAAT2[a] | |
|---|---|---|---|---|---|---|
| Compound | X | Y | Z | R | 4 h | 24 h |
| 7-4 | S | N | N | 2-Me—Bn | 1.7 ± 0.1 | 3.5 ± 0.3 |
| 22 | S | C | N | 2-Me—Bn | 1.3 ± 0.6 | na[b] |
| 8-1 | O | N | N | 2-Me—Bn | 2.0 ± 0.9 | 2.5 ± 0.5 |
| 15 | O | N | C | 2-Me—Bn | 1.5 ± 0.3 | na |
| 7-12 | S | N | N | Bn | 1.3 ± 0.2 | 3.0 ± 0.4 |
| 19 | S | C | C | Bn | 1.2 ± 0.5 | 1.1 ± 0.4 |

[a]Compound concentration of 10 μM;
[b]na = not active

Next, the sulfur linker was examined (Table 3). Replacing the sulfur with oxygen generally yielded less active derivatives. An analogue containing a NH linker (14) showed weaker activity. Likewise, oxidation of the sulfur to a sulfone (9-1, 9-2, and 9-3) was also detrimental. Finally, replacing the sulfur with an amide moiety (17-1 and 17-2) was not tolerated. Collectively, these results indicated that the sulfur linker was optimal.

TABLE 3

Effects of modifications of the sulfur linker on EAAT2 protein levels

| | | | Fold increase for EAAT2[a] | |
|---|---|---|---|---|
| Compound | X | R | 4 h | 24 h |
| 1 | S | 2-Cl-6-F—Bn | na[b] | 2.0 ± 0.8 |
| 8-2 | O | 2-Cl-6-F—Bn | 1.1 ± 0.3 | 2.9 ± 0.4 |
| 7-4 | S | 2-Me—Bn | 1.7 ± 0.1 | 3.5 ± 0.3 |
| 8-1 | O | 2-Me—Bn | 2.0 ± 0.9 | 2.5 ± 0.5 |
| 7-13 | S | 2,6-di-Me—Bn | na | 6.5 ± 1.0 |
| 8-3 | O | 2,6-di-Me—Bn | 2.1 ± 1.2 | 3.2 ± 1.4 |
| 7-14 | S | 1-(2-Cl-6-F-phenyl)ethyl | 1.7 ± 0.9 | 5.5 ± 1.0 |
| 8-4 | O | 1-(2-Cl-6-F-phenyl)ethyl | 1.6 ± 0.2 | 3.0 ± 0.7 |
| 7-15 | S | 2-(2-Cl-6-F-phenylethyl) | 1.9 ± 0.7 | 6.7 ± 1.5 |

TABLE 3-continued

Effects of modifications of the sulfur linker on EAAT2 protein levels

| Compound | X | R | Fold increase for EAAT2[a] 4 h | 24 h |
|---|---|---|---|---|
| 8-5 | O | 2-(2-Cl-6-F-phenylethyl) | 2.2 ± 0.4 | 3.1 ± 1.2 |
| 7-16 | S | 2,4-di-F—Bn | 2.4 ± 1.5 | 3.8 ± 0.8 |
| 8-6 | O | 2,4-di-F—Bn | na | 2.3 ± 0.6 |
| 7-17 | S | 2,4-di-Me—Bn | 1.9 ± 0.8 | 6.4 ± 1.0 |
| 8-7 | O | 2,4-di-Me—Bn | na | 2.0 ± 0.9 |
| 6-1 | S | H | na | 2.0 ± 0.8 |
| 5-1 | O | H | 1.5 ± 0.5 | 1.6 ± 1.0 |
| 14 | NH | 2-Me—Bn | 1.7 ± 1.1 | 2.6 ± 0.5 |
| 9-1 | SO$_2$ | 2-Cl-6-F—Bn | 1.4 ± 0.3 | 2.8 ± 0.4 |
| 9-2 | SO$_2$ | 2-Me—Bn | 2.3 ± 0.4 | 1.1 ± 0.2 |
| 9-3 | SO$_2$ | 2-C—Bn | 1.6 ± 0.3 | na |
| 17-1 | CONH | n-Pr | na | 1.2 ± 0.2 |
| 17-2 | CONH | 2-Me—Bn | na | 1.4 ± 0.2 |
| 27 | C(O)O | i-Pr | na | 1.9 |

[a]Compound concentration of 10 µM;
[b]na = not active

Finally, the benzyl group was examined (Table 4). Compared to 1,2-chloro, 3-chloro and 2,6-dichloro substitutions improved the potency by two-fold (7-7, 7-18 and 7-22), but 2,3-dichloro, 2,4-dichloro and 2,5-dichloro analogues (7-19, 7-21 and 7-20) were equivalent to 1. In the case of fluorine substitutes, only the 2-fluoro and 2,4-difluoro derivatives (7-23 and 7-16) demonstrated improved activity. 4-Fluoro, 2,6-difluoro, and 2,4,6-trifluoro analogues (7-24, 7-25, and 2-26) did not result in significant improvement. Replacement of the halogens with methyls (7-4, 7-13, 7-17, and 7-30) gave increased potency. Compounds containing 2-methyl substituted benzyl groups significantly increased EAAT2 protein level, whereas the 3- or 4-methylbenzyl derivatives (7-27 and 7-28) were less potent. Increasing the tether length between the phenyl and the sulfur to an ethylene generally yielded more potent analogues (7-15 and 7-31 verses 1 and 7-7, respectively) with one noted exception (compare 7-32 to 7-4). However, truncating the linker resulting in a diarylthioether decreased potency (7-29 verses 7-17). Interestingly, adding substitutes on the carbon linker (7-14 and 7-33) increased activity about 3-fold. Finally, other changes gave compounds with essentially the same potency as 1 (7-12, 7-36, and 6-1).

TABLE 4

Effects of the benzyl group on EAAT2 protein levels

| Compound | R | Fold increase for EAAT2[a] 4 h | 24 h |
|---|---|---|---|
| 1 | 2-Cl-6-F—Bn | na[b] | 2.0 ± 0.8 |
| 7-7 | 2-Cl—Bn | 2.1 ± 1.4 | 4.0 ± 0.3 |
| 7-18 | 3-Cl—Bn | 2.1 ± 0.3 | 4.1 ± 0.5 |
| 7-19 | 2,3-di-Cl—Bn | na | 2.4 ± 0.4 |
| 7-20 | 2,5-di-Cl—Bn | 1.4 ± 0.1 | 2.5 ± 0.4 |
| 7-21 | 2,4-di-Cl—Bn | 1.8 ± 0.5 | na |
| 7-22 | 2,6-di-Cl—Bn | 1.5 ± 0.8 | 3.9 ± 0.4 |
| 7-23 | 2-F-Bn | 2.2 ± 0.1 | 3.1 ± 0.2 |
| 7-24 | 4-F-Bn | 2.5 ± 0.6 | 2.6 ± 0.3 |
| 7-16 | 2,4-di-F—Bn | 2.4 ± 1.5 | 3.8 ± 0.8 |
| 7-25 | 2,6-di-F—Bn | 2.1 ± 1.4 | 2.2 ± 0.7 |
| 7-26 | 2,4,6-tri-F—Bn | 1.6 ± 1.0 | 2.4 ± 0.6 |
| 7-4 | 2-Me—Bn | 1.7 ± 0.1 | 3.5 ± 0.3 |
| 7-27 | 3-Me—Bn | 2.0 ± 0.2 | 2.8 ± 0.5 |
| 7-28 | 4-Me—Bn | 2.1 ± 1.1 | 2.6 ± 0.4 |
| 7-29 | 2,4-di-Me—Ph | 1.2 ± 0.3 | 2.2 ± 0.3 |
| 7-17 | 2,4-di-Me—Bn | 1.9 ± 0.8 | 6.4 ± 1.0 |
| 7-13 | 2,6-di-Me—Bn | na | 6.5 ± 1.0 |
| 7-30 | 2,4,6-tri-Me—Bn | 1.7 ± 0.3 | 4.7 ± 0.5 |
| 7-15 | 2-(2-Cl-6-F-phenylethyl) | 1.9 ± 0.7 | 6.7 ± 1.5 |
| 7-31 | 2-(2-Cl-phenylethyl) | 1.7 ± 0.2 | 4.8 ± 0.6 |
| 7-32 | 2-(2-Me-phenylethyl) | 1.2 ± 0.3 | 2.8 ± 0.4 |
| 7-33 | 1-(1,2,3,4-tetrahydronaphthalenyl) | na | 5.3 ± 1.1 |
| 7-14 | 1-(2-Cl-6-F-phenyl)ethyl | 1.7 ± 0.9 | 5.5 ± 1.0 |
| 7-34 | 2-Cl-4-F—Ph | 1.3 ± 0.1 | 2.5 ± 0.7 |
| 7-35 | 2-Cl-4-F—Bn | 1.6 ± 0.6 | 1.7 ± 0.4 |
| 7-12 | Bn | 1.3 ± 0.2 | 3.0 ± 0.5 |
| 7-36 | Et | 1.6 ± 0.7 | 1.9 ± 0.9 |
| 6-1 | H | na | 2.0 ± 0.8 |
| 26 | | na | 6.4 |

[a]Compound concentration of 10 µM;
[b]na = not active

Example 2

ALS Model (SOD1(G93A) Mouse Model)

Guidelines established by the ENMC Group were followed (see Ludolph, A. C., et al. Guidelines for the preclinical in vivo evaluation of pharmacological active drugs for ALS/MND: report on the 142nd ENMC international workshop. Amyotroph Lateral Scler 8, 217-223 (2007))[1], which included the use of gender matched mice (i.e. equal number of males and females in each experimental group), use of littermate matched mice (i.e. the littermate of a therapeutic mouse is used in the control group) and use of mice with the same copy number of the SOD1 transgene. SOD1(G93A) mice received Compound 212320 (shown below, shown also as compound 7-4 in FIG. 1) at 40 mg/kg in 500 µl of 1% DMSO/1% polyethylene glycol 400/0.2% Tween 80/10% hydroxypropyl-β-cyclodextrin/saline starting at 84 days of age (6 times/week, at the same time each day) until death or harvested at 120-days of age for analysis. Western blotting, cresyl violet staining and immunofluorescence staining were performed as previously described in Chang, Y., et al. Messenger RNA oxidation occurs early in disease pathogenesis and promotes motor neuron degeneration in ALS. PLoS One 3, e2849 (2008).

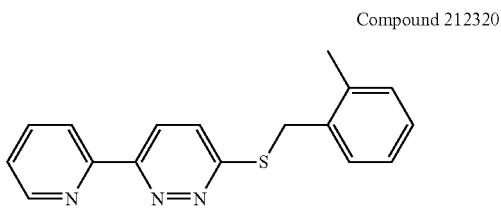 [SMILES: Cc1ccccc1CSc1ccc(-c2ccccn2)nn1]

Compound 212320

Motor function was determined by measuring peak force using a digital grip dynamometer outfitted with a hind limb pull bar assembly (Columbus Instruments). Measurements started from 70 days of age (three times a week, on the same day of each week and at the same time of each scheduled day) until the mouse loses all strength. Six repetitions were conducted and the average was determined for each point. The examiners were unaware of the treatment of the mice. Food and water were placed on the cage floor when mice began to show motor deficits. Mice were euthanized when they were unable to roll over within 30 seconds after being placed on their sides. This time point was recorded as the time of death for survival in days.

Figure 2:
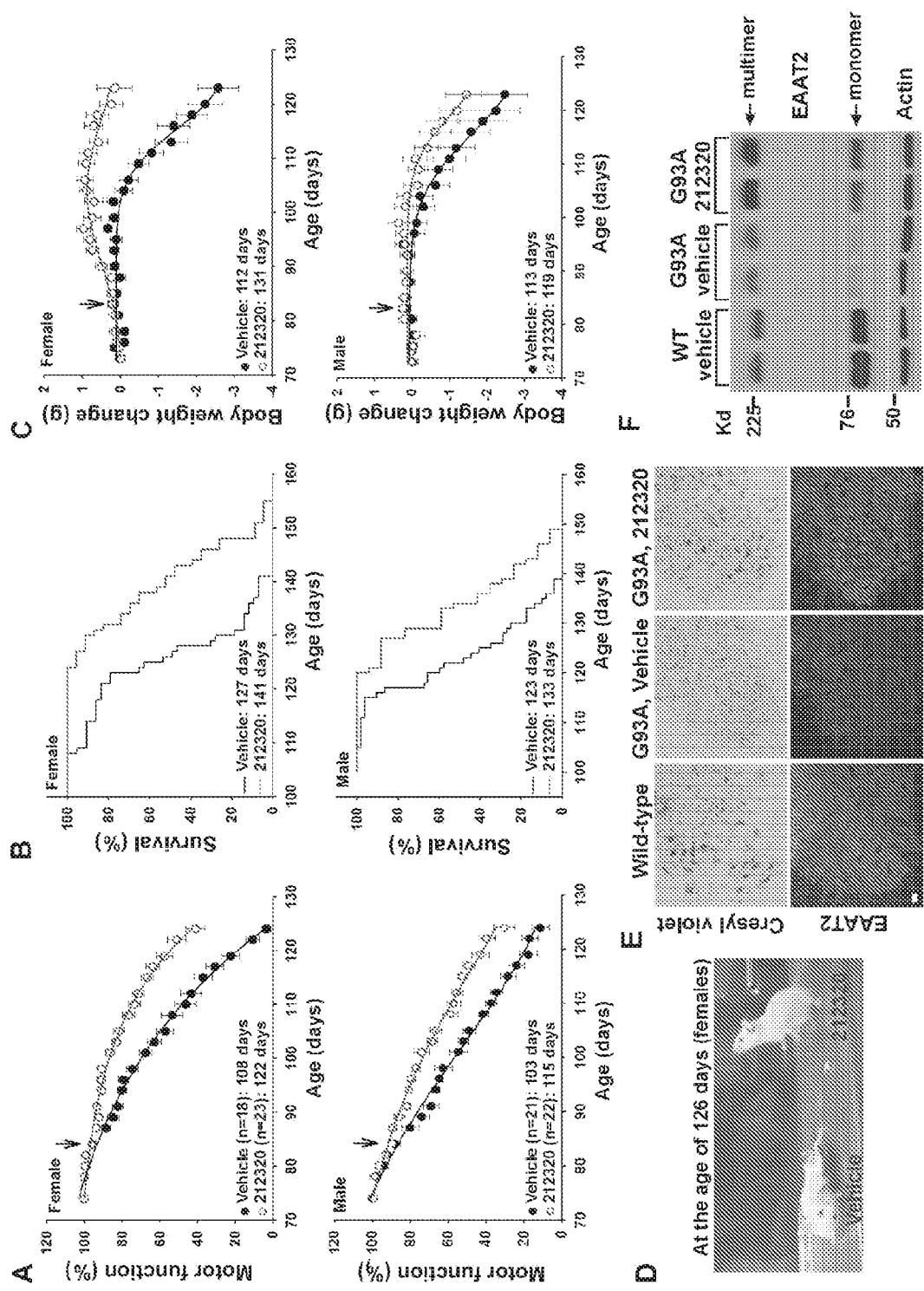
FIGS. 2A-2F are graphs and phographs showing the effect of an exemplary compound in a mouse model for ALS.

Results are shown in FIG. 2. Referring to FIG. 2, Compound 212320 delayed motor function decline and extended life span in SOD1(G93A) mice. SOD1(G93A) mice received compound 7-4, daily (i.p., 40 mg/kg) starting at 84 days of age (arrows indicated in the figure) until death. FIG. 2(A) shows motor function decline as assessed by grip strength measurement. Data were analyzed using the dynamic fitting nonlinear regression analysis. The average days of 50% grip strength decline are indicated. FIG. 2(B) shows survival results. Data were analyzed using Kaplan-Meier survival analysis. The average survival days are indicated. FIG. 2(C) shows body weight change. The average days of 10% decline of initial body weight are indicated. FIG. 2(D) shows represented female mice at the age of 126 days. FIG. 2(E) shows represented images showing cresyl violet staining and EAAT2 immunostaining of the ventral horn region of the spinal cord from female mice at age of 120 days. FIG. 2(G) shows western blot results, which show Compound 212320 restores EAAT2 protein levels. Spinal cords from 120-day-old mice were analyzed.

Example 3

Epilepsy Model (Pilocarpine-Induced Status Epilepticus (SE) Mouse Model)

Eight- to ten-week-old male FVB mice (22-32 g) received the $1^{st}$ and $2^{nd}$ injections of Compound 212320 (at 40 mg/kg in the formulation described above) at 20 and 3 hr prior to induction of seizure with pilocarpine (290 mg/kg, i.p., Sigma). To reduce peripheral cholinergic effects without interfering with the development of SE and chronic seizures, mice received (−) scopolamine methyl nitrate (1.5 mg/kg, Sigma, St. Louis, Mo.) 30 min prior to pilocarpine injection. Control animals were injected with scopolamine followed by saline, instead of pilocarpine. Mice were then observed for 2 hr to record acute seizure severity and latency period. The Racine scale (see Racine, R. J. Modification of seizure activity by electrical stimulation. II. Motor seizure. *Electroencephalogr Clin Neurophysiol* 32, 281-294 (1972)) was used to rate seizure severity as previously described in Kong, Q., et al. Increased glial glutamate transporter EAAT2 expression reduces epileptogenic processes following pilocarpine-induced status epilepticus. Neurobiol Dis (2012)).

Mice that reached SE and maintained tonic limbic extension for at least 60 min were kept and treated with compound daily for chronic seizure and pathological studies. The SE mice were fed with food soaked in a high sucrose (10%) saline solution to help recovery in the first 3 days after SE. Vehicle-treated SE mice and compound-treated SE littermates were carefully matched based on the body weight, seizure latency, seizure severity, and post-SE sickness. Therefore, the nature of the SE (i.e. seizure length and severity) in those mice was comparable.

Figure 3:
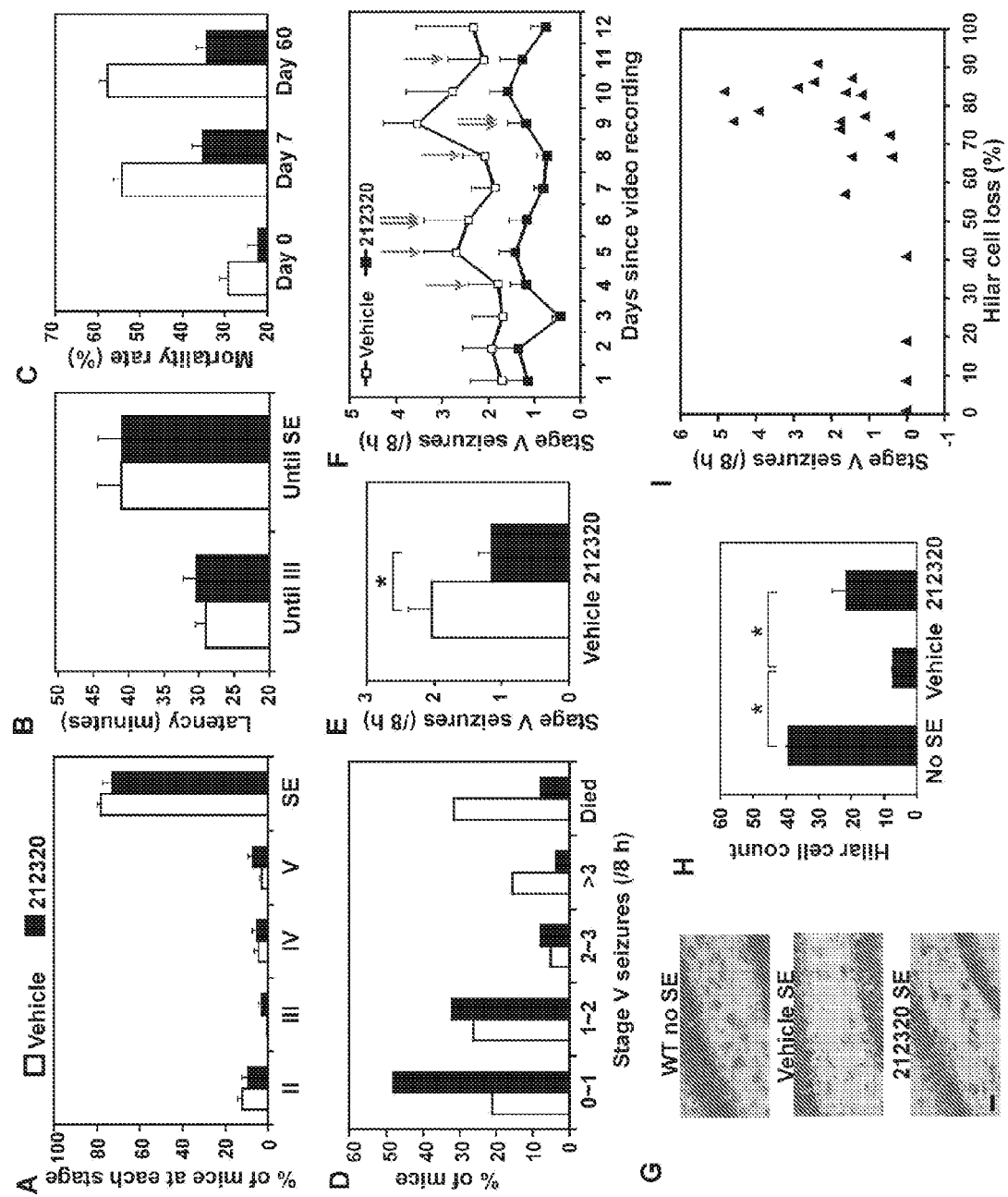
FIGS. 3A-3I are graphs and photographs showing the effect of an exemplary compound in a mouse model for epilepsy.

Chronic seizure activities were recorded by webcam (Logitech, Fremont, Calif.) and reviewed using Windows Live Movie Maker. Daylight periods (9 AM-5 PM) were selected for observations because previous literature indicates a higher frequency of spontaneous recurrent seizures during the day (see Kong, Q., et al. Increased glial glutamate transporter EAAT2 expression reduces epileptogenic processes following pilocarpine-induced status epilepticus. Neurobiol Dis (2012); and Shapiro, L. A., Figueroa-Aragon, S. & Ribak, C. E. Newly generated granule cells show rapid neuroplastic changes in the adult rat dentate gyrus during the first five days following pilocarpine-induced seizures. Eur J Neurosci 26, 583-592 (2007)). At 8 weeks post-SE, brain tissue was harvested from SE mice for cresyl violet staining Results are shown in FIG. 3. Referring to FIG. 3, Compound 212320 reduced mortality rate, spontaneous recurrent seizure and neuronal death following pilocarpine-induced SE. Adult male FVB mice received Compound 212320 (i.p., 40 mg/kg), 3-hr later, were induced seizures with pilocarpine and were then observed for 2 hr to record acute seizure severity and latency period. The Racine scale was used to rate the seizure severity (described above). Mice that reached SE were treated with compound daily and at 4-week post-SE, were recorded chronic seizures for 2 weeks. A total of 15 independent experiments were performed, with a total of 153 vehicle-treated mice and 152 compound 7-4-treated mice. FIG. 3(A) shows acute seizure severity (the maximal seizure activity of each animal within 2-hr after pilocarpine injection). The percentage of mice that reached each seizure stage was not significantly different between vehicle group and compound group (n=15 groups). FIG. 3(B) shows latency (the time interval between pilocarpine injection and the indicated stage). The latencies were not significantly different between the two groups. FIG. 3(C) shows Mortality rate (the percentage of mice that died in each group of mice). There was no obvious difference between the two groups on the day that SE was induced but significantly decreased in compound groups on day 7 post-SE and also on day 60 post-SE. FIGS. 3(D-F) show spontaneous recurrent seizure. FIG. 3(D) shows the percentages of mice (in 19 vehicle- and 25 compound 7-4-treated mice) that developed <1, 1~2, 2~3, or >3 stage V seizures per 8 hr. FIG. 3(E) shows the average stage V seizure frequencies per 8 hr (*p<0.05). FIG. 3(F) shows the stage V seizure frequencies during each day of the recording. The chronic seizure frequency was significantly reduced in compound-treated mice. FIGS. 3(G-H) show hippocampal damage. Nine sets of brains at 8 weeks post-SE were analyzed with cresyl violet staining FIG. 3(G) shows represented images of dentate hilus. FIG. 3(H) shows quantitative analysis of the numbers of hilar cell. Compared to control brains, both vehicle- and compound-treated SE brains had significant neuronal loss in hilus but compound treatment significantly attenuated the damages (*p<0.05). FIG. 3(I) shows a strong positive correlation was detected between hilar cell loss and chronic seizure frequencies.

Example 4

Stroke Model

Compound 212320 was evaluated in the transient middle cerebral artery occlusion (MCAO), a well-characterized model of focal cerebral ischemia (experimental stroke). Adult male C57/BL6 mice (60-70 days old) were used. The internal carotid artery was occluded for 60 min. Following reperfusion, mice received 40 mg/kg of Compound 212320 by intraperitoneal injection. 24 hours after surgery, brains were removed and processed to determine infarct volume. A 57% decrease of infarct volume was observed in Compound 212320-treated mice (vehicle: 15.9±8.1; compound: 6.8±1.6; n=6 each) (FIG. 3). This study indicates that Compound 212320 can have protective effects in this focal cerebral ischemia model.

Figure 4:
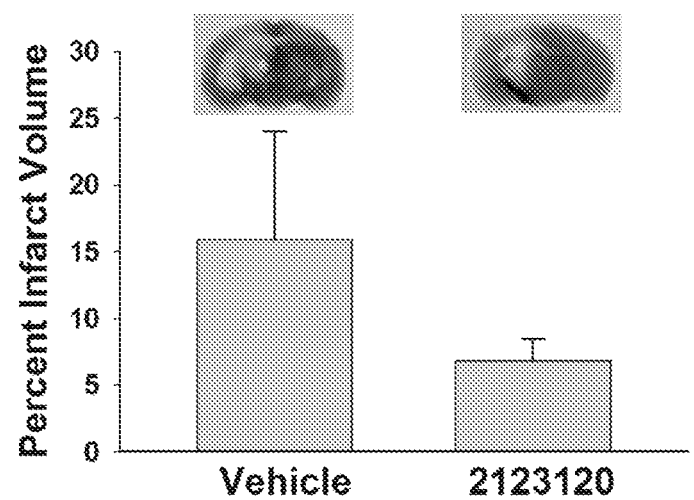
FIG. 4 is a graph showing the effect of an exemplary compound in a mouse model for focal cerebral ischemia.

FIG. 4 demonstrates the efficacy of Compound 212320 in the transient middle cerebral artery occlusion (MCAO) model for stroke. Mice received 40 mg/kg Compound 212320 or vehicle intraperitoneally and 24 h after stroke, brains were processed to measure infarct volume.

Example 5

Alzheimer's Disease Model

Compound 212320 was evaluated in $APP_{Sw/Ind}$ transgenic mice, an Alzheimer's disease model. These $APP_{Sw/Ind}$ mice exhibit loss of learning and memory beginning from the age of 4-5 months. 7-month-old mice were treated with 40 mg/kg of Compound 212320 by intraperitoneal injection daily for 10 days and then evaluated the effects on short-term memory by Y-maze test. Compound 212320 restored short-term memory loss in APP mice after 10-day treatment (23 wild-type mice, 21 APP mice). This study indicates that Compound 212320 can have protective effects in this Alzheimer's model.

Figure 5:
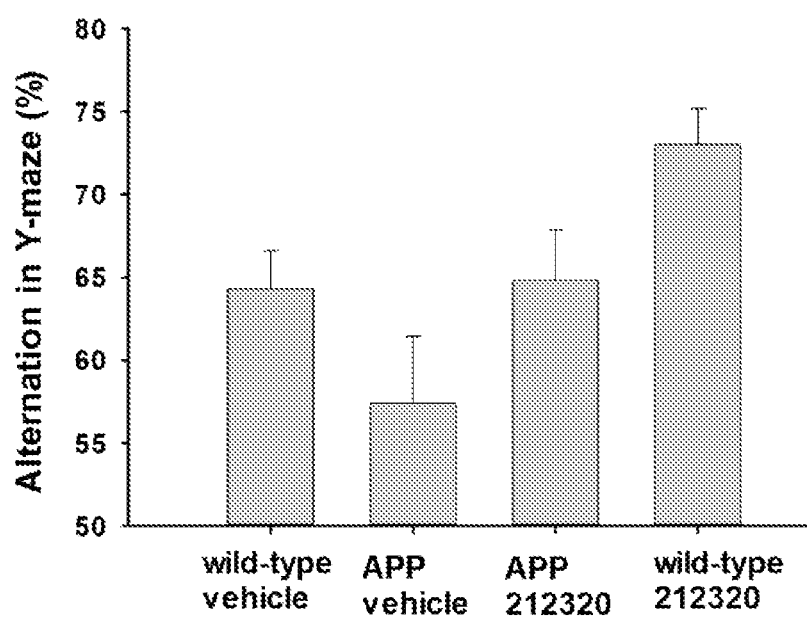
FIG. 5 is a graph showing the effect of an exemplary compound in a mouse model for Alzheimer's disease.

FIG. 5 demonstrates the efficacy of Compound 212320 in a mouse model for Alzheimer's disease. $APP_{Sw/Ind}$ transgenic mice were treated with Compound 212320 at 40 mg/kg or vehicle intraperiotoneally beginning at 7 months after symptoms of memory loss are apparent. After daily treatment for 10 days, Y-maze was used to measure effects on short-term memory.

Example 6

Figure 6:
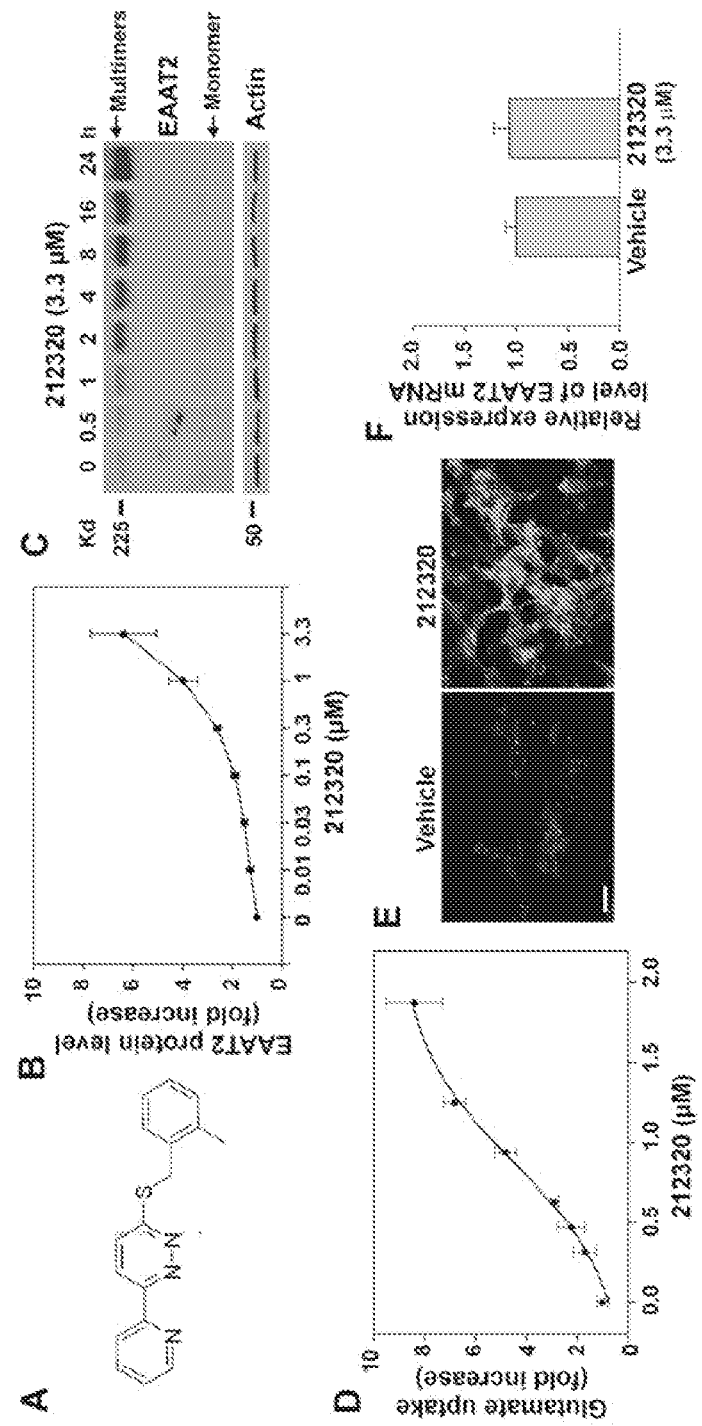
FIGS. 6A-6F are chemical structures, graphs, and photographs showing the characterization of an exemplary compound in PA-EAAT2 cells.

Functional Activation of EAAT2 by Compound 212320 in a Primary Astrocyte Cell Line, Primary Dissociated Neuron and Astrocyte Mixed Cultures, and Wild-Type Mice Characterization and efficacy studies of a compound, Compound 212320 (FIG. 6A) is shown. PA-EAAT2 is a rat primary astrocyte line that did not express endogenous EAAT2 protein but stably expressed human EAAT2 mRNAs driven by the CMV promoter. In the absence of serum, PA-EAAT2 cells express low amounts of EAAT2 protein, although the recombinant EAAT2 mRNA are expressed (translational silencing); however, EAAT2 protein levels are increased when an activator is added to the culture (translational activation). This cell line was used for high-throughput screening to identify EAAT2 translational activators. To prioritize candidate compounds, we initially evaluated activation of EAAT2 protein in PA-EAAT2 cells. Promising compounds were further evaluated in primary dissociated neuron and astrocyte mixed cultures and then in mice. FIG. 6 presents the characterization of Compound 212320 in PA-EAAT2 cells. Compound 212320 increased EAAT2 protein levels in a dose—(FIG. 6B) and time—(FIG. 6C) dependent manner. Importantly, the induction occurred in a short amount of time (within 1-2 hr) and was sustained even up to 72 hr (data not show). Additionally, induction occurred at low nanomolar concentrations. A [$^3$H]glutamate uptake assay demonstrated that glutamate uptake function correlated to increased EAAT2 protein levels. (FIG. 6D). Immunofluorescent staining showed that induced EAAT2 protein was properly localized to the plasma membrane (FIG. 6E). Quantitative real-time RT-PCR analysis revealed that EAAT2 mRNA levels were not changed by Compound 212320 (FIG. 6F), suggesting that the increased EAAT2 protein levels resulted from an increase in translation.

Figure 7:
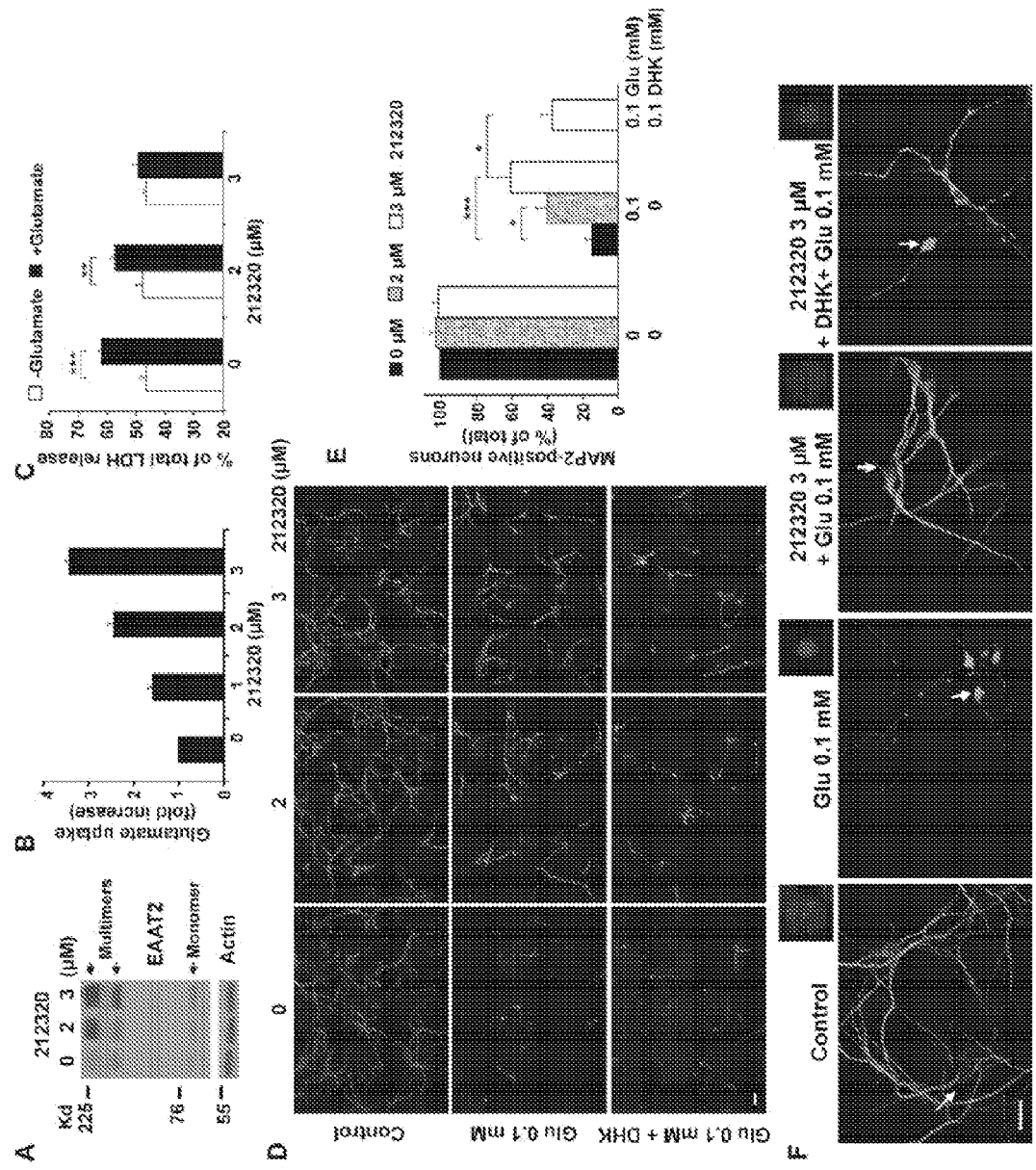
FIGS. 7A-7F are graphs and photographs showing data from an evaluation of an exemplary compound in primary dissociated neuron and astrocyte mixed cultures.

We next evaluated Compound 212320 in primary dissociated neuron and astrocyte mixed cultures. Seven day-old cultures were treated with Compound 212320 in serum-free media for 48 hr. As shown in FIG. 7A-B, Compound 212320 increased EAAT2 protein levels and glutamate uptake function. Significantly, when the cultures were treated with glutamate for 2 hr to induce excitotoxicity, the Compound 212320-treated cultures were protected. FIG. 7C shows that glutamate-induced cytotoxicity as assessed by the LDH assay was significantly reduced by Compound 212320. FIG. 7D shows that Compound 212320 treatment significantly prevented neuronal loss and degeneration as assessed by MAP2 immunostaining. On average, 14.6±4.4% of MAP2-positive neurons were left after 0.1 mM glutamate treatment when compared to the control, while pretreatment with Compound 212320 at 2 or 3 µM significantly recovered this ratio to 40.4±6.4% and 60.9±7.3%, respectively (FIG. 7E). These protective effects were partially abolished by pretreatment with dihydrokainic acid (DHK), an EAAT2 blocker, suggesting that activation of EAAT2 is involved in Compound 212320-mediated neuroprotection. FIG. 7F shows MAP2 immuno labeling and nuclear condensation (arrows) at a higher magnification. Furthermore, in all assays, Compound 212320 did not cause any detectable toxicity.

Figure 8:
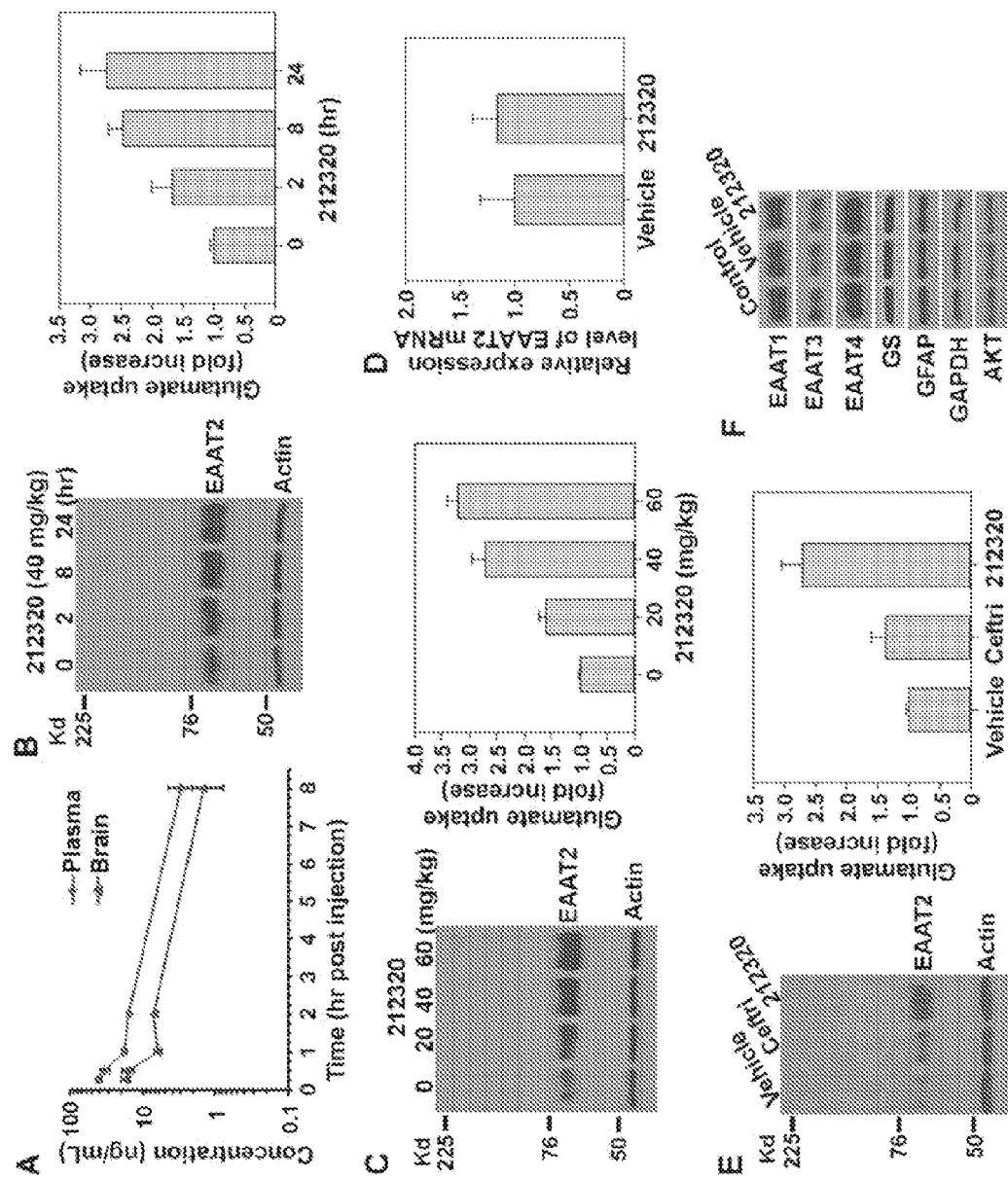
FIGS. 8A-8F are graphs and photographs showing data from in vivo pharmacokinetic evaluation of an exemplary compound in male C57Bl/6 mice.

Compound 212320 is compliant with Lipinski rules and lacks functionality that would predict overt toxicity or reactivity. This compound has a low molecular weight (293.38), cLogP value (3.28) and polar surface area (PSA) value (37.08 Å2) in the range typical of compounds that can penetrate the blood brain barrier. We conducted in vivo pharmacokinetic evaluation of LDN 212320 in male C57Bl/6 mice. After a single intraperitoneal (i.p.) administration of Compound 212320 (3 mg/kg), the plasma and brain concentrations were determined over an 8 hr period by LCMS/MS (FIG. 8A). Compound 212320 reached an average $C_{max}$ of 42.1±3.6 ng/mL at 15 min post-injection. The plasma and brain half-lives were estimated to be 2.63 and 2.64 hr, respectively. The average brain-to-plasma ratio was approximately 2 at all time points tested. These results indicate that Compound 212320 has adequate pharmacokinetic properties.

We determined maximum tolerated dose (MTD) of Compound 212320 in male C57BL/6 mice. The study was conducted in two phases: (I) a single dose tolerability study tested at the doses of 10, 25, 50, and 75 mg/kg i.p. (3 mice/dose) and (II) a five-day repeat-dose tolerability study tested at the doses of 10, 25, 50, and 100 mg/kg i.p. (5 mice/dose). All animals were observed for clinical signs of toxicity each day of dosing. In the repeat-dose study, body weights were determined prior to each dose and prior to termination on day 6. Clinical pathologies including standard hematology, serum chemistry and coagulation parameters were evaluated on samples collected on day 6. All animals from phase II were necropsied, and selected organs were weighed. There were no clinical signs of toxicity, adverse clinical pathology changes, or body weight changes relative to controls at the end of dosing. Due to lack of toxicity, the highest dose tested, 100 mg/kg/day, was determined to be the 5-day no observed adverse effect level (NOAEL) for Compound 212320.

We next examined EAAT2 protein levels and glutamate uptake activities in brain following i.p. administration of Compound 212320 in C57BL/6 mice. Plasma membrane vesicles were prepared from mouse forebrains to measure functional EAAT2 protein. After a single i.p. dose of Compound 212320 at 40 mg/kg, EAAT2 protein levels and associated glutamate uptake increased to ~1.5-2-fold at 2 hr and to ~2-3-fold from 8 hr to 24 hr post-injection (FIG. 8B). Even at 72 hr, a ~1.5 fold increase in EAAT2 protein levels could still be detected (data not shown). In addition, Compound 212320-induced EAAT2 protein levels and glutamate uptake were both dose-dependent (FIG. 8C). This induction was not due to transcriptional activation because EAAT2 mRNA was not increased as measured by quantitative real-time RT-PCR (FIG. 8D). We compared ceftriaxone (200 mg/kg), which increases EAAT2 expression through transcriptional activation, with Compound 212320 (40 mg/kg) that activates EAAT2 translation. As shown in FIG. 8E, Compound 212320 had greater EAAT2 induction than ceftriaxone (a single dose after 24 hr).

These results indicate that Compound 212320 has good potency in vivo. To assess Compound 212320's biological activity and selectivity, we performed an in vitro side effect profiling study. Seventy-one targets were tested at 10 μM in duplicate. These targets include neurotransmitter related receptors (30), steroids (2), ion channels (6), second messenger (1), prostaglandins (3), growth factors/hormones (4), brain/gut peptides (13), enzymes (5) and cytochrome p450 (7). The results showed that Compound 212320 had 69% inhibition on the cytochrome p450 CYP1A2 and 43% inhibition on calcium channel L-type at 10 μM. All other targets demonstrated <30% inhibition at 10 μM. Additionally, we performed a protein kinase profiling study. Compound 212320 was tested at 1 and 10 μM against 288 kinases. The results showed that EphA4 and EphA5 were inhibited by 44% at 10 μM. All other kinases tested showed insignificant activity. These studies indicate that Compound 212320 has high specificity and low side-effects/toxicity potential.

Furthermore, the following observations indicate that the effects of Compound 212320 on EAAT2 protein expression were not due to a general increase in protein synthesis. First, the total amount of protein in compound-treated cells and mice was not increased compared with that in vehicle-treated cells and mice. Secondly, we examined the expression of a variety of other proteins in mouse brains: astrocyte-specific proteins including GFAP, glutamine synthetase (GS), and EAAT1 (another astrocytic glutamate transporter subtype), several housekeeping proteins including GAPDH, SOD1, actin, YB-1, RNA polymerase II, several neuronspecific proteins including synaptophysin, EAAT3 (a neuronal glutamate transporter), EAAT4, PSD95, and several signaling proteins including AKT, PI3K, IkB-α and ERK2. None of the above proteins were induced by Compound 212320 (FIG. 8F), suggesting that Compound 212320 did not induce global protein synthesis.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for treating a disease, disorder, or condition in a subject in need thereof, wherein the disease, disorder, or condition is selected from the group consisting of ischemic stroke, epilepsy, trauma, Parkinson's disease, Alzheimer's disease, multiple sclerosis, mesial temporal sclerosis, Huntington's disease, AIDS dementia complex, amyotrophic lateral sclerosis (ALS), migraine, temporomandibular disorders, neuropathic pain, visceral pain, complex regional pain syndrome, alcohol addiction, drug addiction, a cancer, and depression, the method comprising administering to the subject an effective amount of a compound of formula (I), or a pharmaceutically acceptable salt thereof:

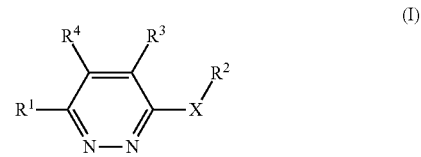

wherein:
$R^1$ is pyridyl or phenyl, each of which is optionally substituted with from 1-5 independently selected $R^a$;
X is S, S(O), SO$_2$, O, N(C$_1$-C$_3$ alkyl), C(O)O, C(O)NH, C(O)NHCH$_2$, C$_1$-C$_4$ alkylene, or a bond;
$R^2$ is:
(i) —Y—$R^5$, wherein Y is C$_1$-C$_8$ alkylene or a bond; and $R^5$ is independently selected from: (a) phenyl which is optionally substituted with from 1-5 independently selected $R^b$, and (b) heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-5 independently selected $R^b$, (c) C$_1$-C$_8$ alkyl, (d) H; or
(ii) C$_9$-C$_{12}$ aryl-cycloalkyl, wherein the aryl portion is optionally substituted with from 1-5 independently selected $R^b$; or heteroaryl-cycloalkyl, which contains from 9-12 ring atoms, wherein from 1-4 of the ring atoms is independently selected from N, NH, N(C$_1$-C$_3$ alkyl), O, and S; and wherein said heteroaryl portion is optionally substituted with from 1-3 independently selected $R^b$;
each of $R^3$ and $R^4$ is independently selected from hydrogen and C$_1$-C$_3$ alkyl;
$R^a$ at each occurrence is, independently, selected from halo, —OH, C$_1$-C$_6$ alkoxy, C$_1$-C$_6$ thioalkoxy, C$_1$-C$_6$ haloalkoxy, C$_1$-C$_6$ thiohaloalkoxy, C$_1$-C$_6$ alkyl, C$_1$-C$_6$ haloalkyl, and —CN; and
$R^b$ at each occurrence is independently selected from any of the substituents delineated in (a) (b), (c), (d), (e), and (f), inclusive, below:
(a) halo;
(b) C$_1$-C$_6$ alkyl or C$_1$-C$_6$ haloalkyl, each of which is optionally substituted with —NH(C$_1$-C$_6$ alkyl), N(C$_1$-C$_6$ alkyl)$_2$, —NHC(O)(C$_1$-C$_6$ alkyl);
(c) —OH; C$_1$-C$_6$ alkoxy; C$_{2-8}$ alkynyloxy, C$_1$-C$_6$ haloalkoxy; C$_1$-C$_6$ thioalkoxy; C$_1$-C$_6$ thiohaloalkoxy; —NH$_2$; azido; —NH(C$_1$-C$_6$ alkyl), N(C$_1$-

$C_6$ alkyl)$_2$, —NHC(O)($C_1$-$C_6$ alkyl), wherein the alkyl portion of each is optionally substituted with cyano;
(d) $C_3$-$C_6$ cycloalkyl or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and wherein each of said cycloalkyl and heterocyclyl is optionally substituted with from 1-3 independently selected $C_1$-$C_4$ alkyl groups;
(e) $C_2$-$C_4$ alkenyl; $C_2$-$C_8$ alkynyl;
(f) nitro; cyano; —C(O)H; —C(O)($C_1$-$C_6$ alkyl); C(O)OH; —C(O)O($C_1$-$C_6$ alkyl); —C(O)NH$_2$—SO$_2$($C_1$-$C_6$ alkyl); —SO$_2$($C_1$-$C_6$ haloalkyl); —C(O)NR'''R''''—SO$_2$NR'''R'''', —SO$_2$NH$_2$, —NHCO($C_1$-$C_6$ alkyl), —NHSO$_2$($C_1$-$C_6$ alkyl), whereby R''' and R'''' is independently selected from H, $C_1$-$C_6$ alkyl, $C_1$-$C_6$ haloalkyl.

2. The method of claim 1, wherein $R^1$ is 2-pyridyl.
3. The method of claim 1, wherein X is S, S(O), SO$_2$; O, N($C_1$-$C_3$ alkyl), or a bond.
4. The method of claim 1, wherein X is CH$_2$.
5. The method according to claim 1, wherein $R^2$ is —Y—$R^5$.
6. The method of claim 5, wherein Y is $C_1$-$C_8$ alkylene.
7. The method of claim 1, wherein $R^5$ is independently selected from:
(a) phenyl, which is optionally substituted with from 1-5 independently selected $R^b$, and (b) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-5 independently selected $R^b$.
8. The method of claim 5, wherein $R^5$ is phenyl, which is optionally substituted with from 1-5 independently selected $R^b$.
9. The method of claim 8, wherein $R^b$ is $C_1$-$C_6$ alkyl or halo.
10. The method of claim 8, wherein $R^5$ has the following formula:

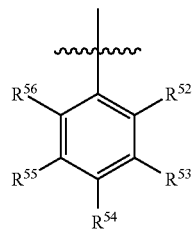

wherein 1, 2, or 3 of $R^{52}$, $R^{53}$, $R^{54}$, $R^{55}$, and $R^{56}$ is/are an independently selected $R^b$, and the others are hydrogen.
11. The method of claim 10, wherein one of $R^{52}$ and $R^{56}$ is $R^b$, and the other of $R^{52}$ and $R^{56}$ is an independently selected $R^b$ and/or $R^{54}$ is an independently selected $R^b$.
12. The method according to claim 10, wherein each occurrence of $R^b$ is an independently selected $C_1$-$C_6$ alkyl, a fluoro, or a chloro.
13. The method according to claim 8, wherein $R^5$ is:
2-methylphenyl,
2-chlorophenyl,
2, 6-dimethylphenyl,
2, 4-dimethylphenyl,
2, 6-dichlorophenyl,
2-fluorophenyl,
2,4-difluorophenyl,
3-chlorophenyl,
2,4,6,-trimethylphenyl,
2-chloro-6-fluorophenyl,
2,3-dichlorophenyl,
2,4-dichlorophenyl,
2,5-dichlorophenyl,
2,6-difluorophenyl,
2,4,6,-trifluorophenyl,
4-fluorophenyl,
2-chloro-4-fluorophenyl,
3 -methylphenyl,
2-azido-4-(hex-5-yn-1 -yloxy)phenyl,
6-methylpyridin-2-yl,
isopropyl, or
4-methylphenyl.
14. The method according to claim 1, wherein $R^2$ is $C_9$-$C_{12}$ aryl-cycloalkyl, wherein the aryl portion is optionally substituted with from 1-5 independently selected $R^b$.
15. The method according to claim 1, wherein the compound of formula (I) is selected from the group consisting of:

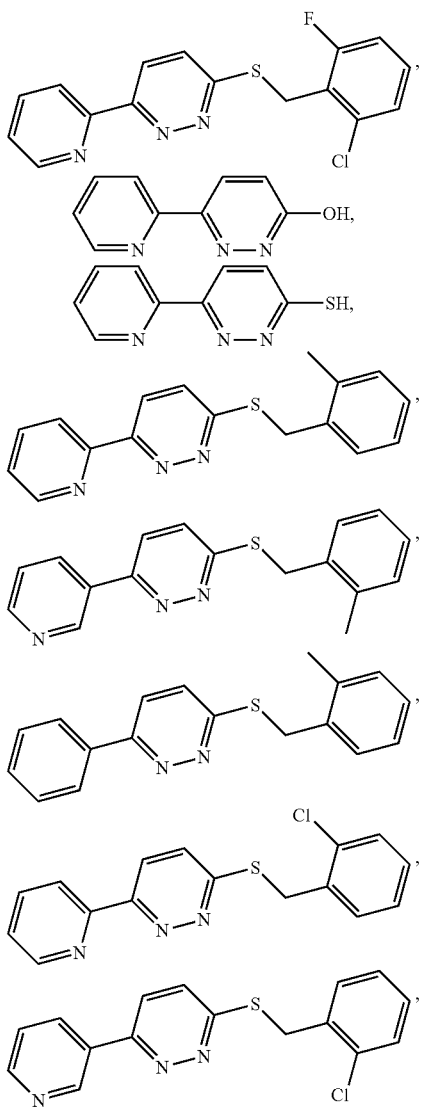

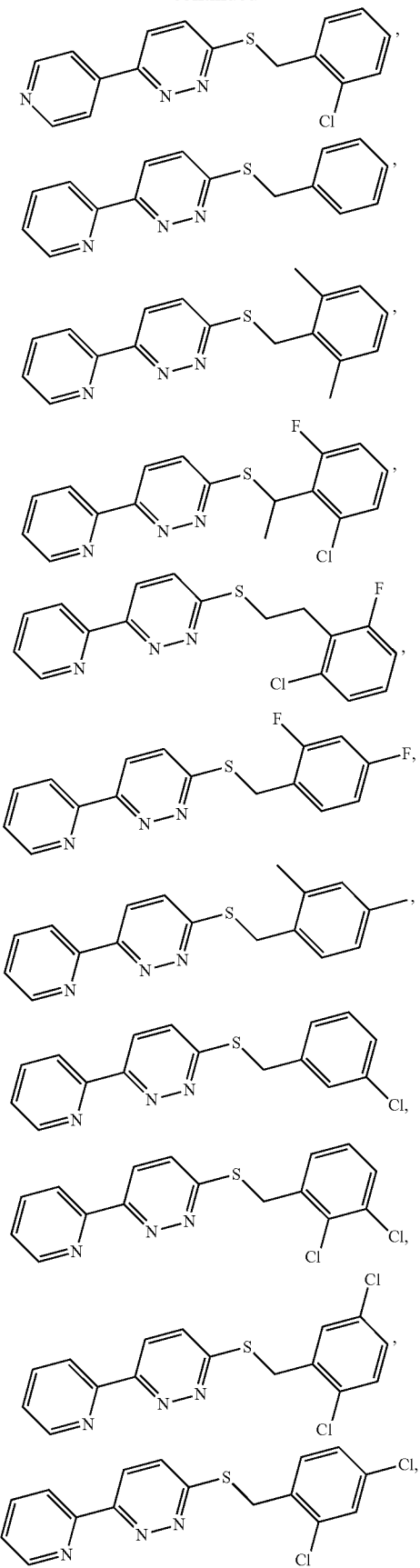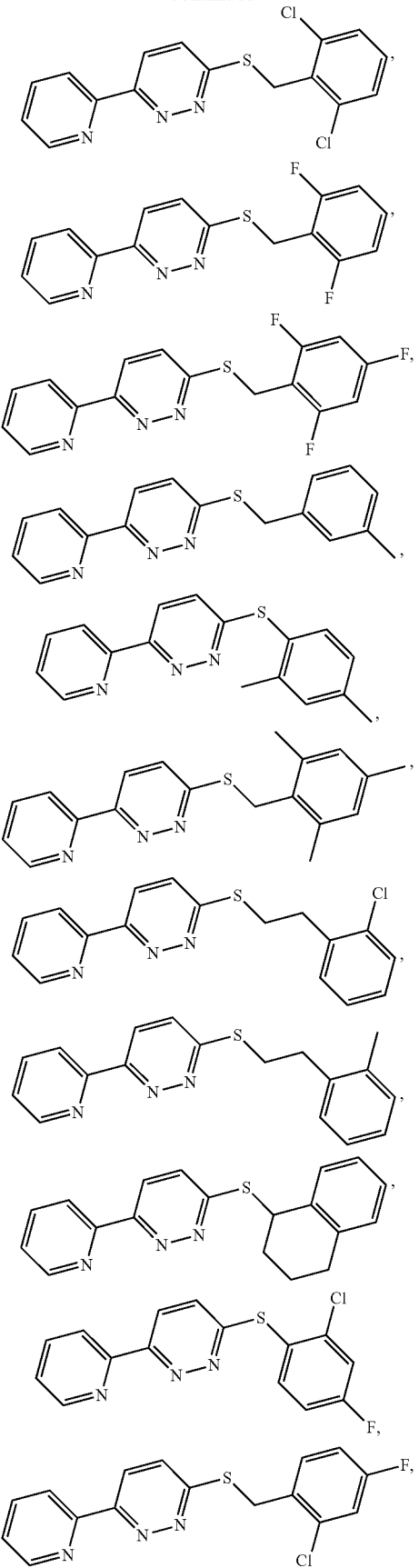

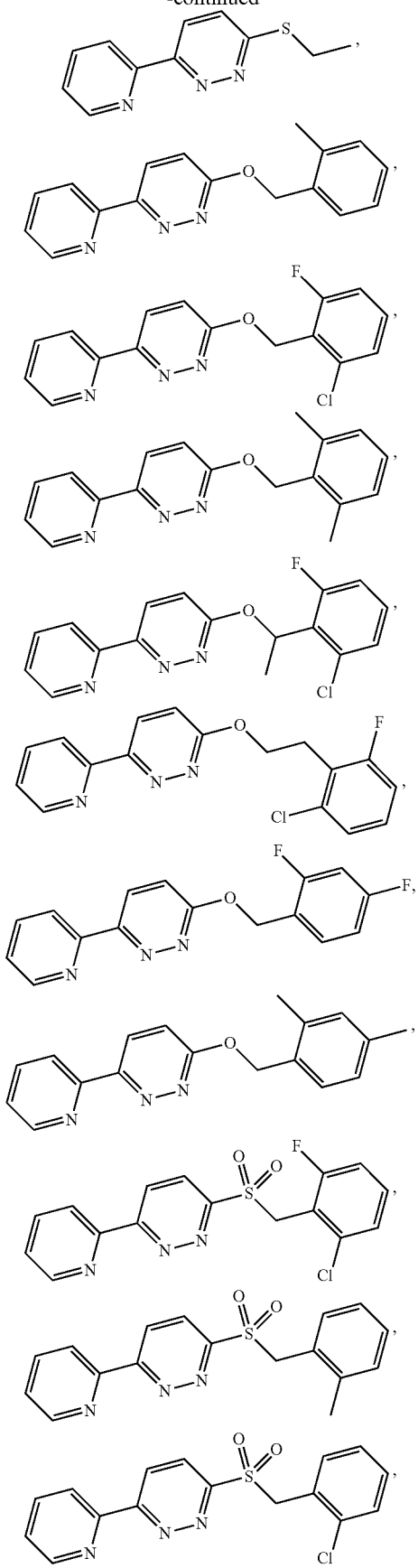
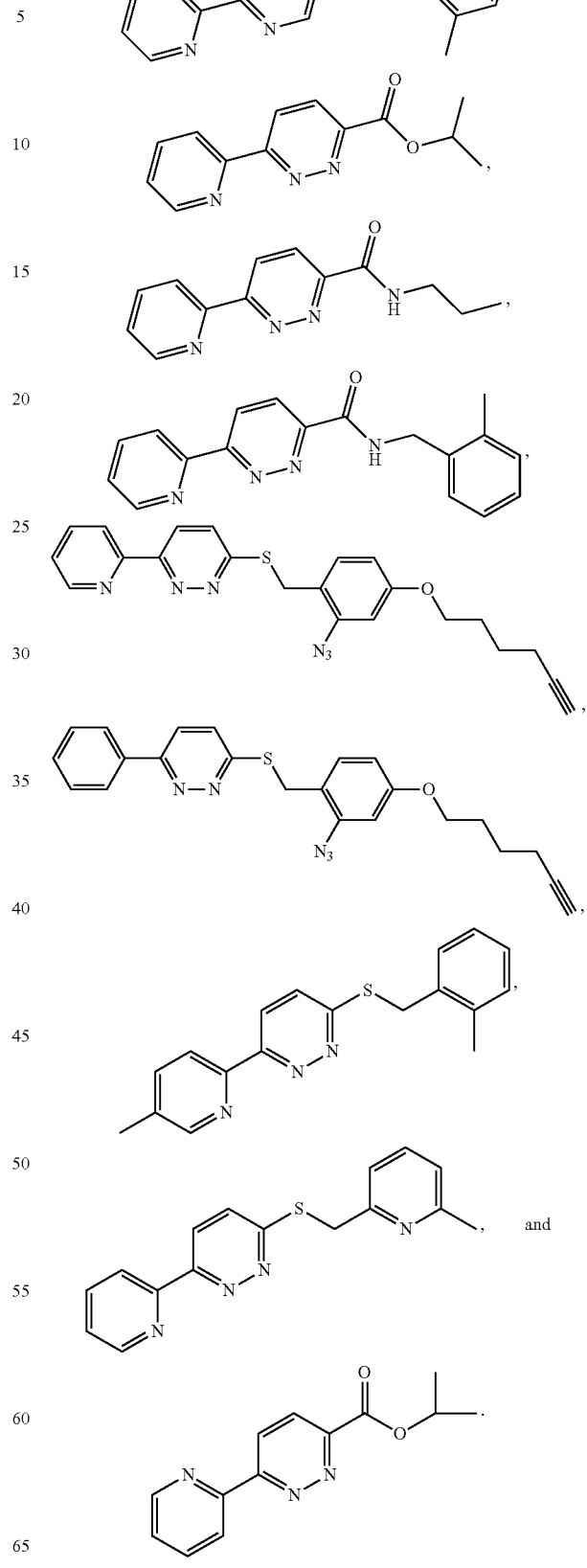

16. The method of claim 1, wherein the disease, disorder, or condition is selected from the group consisting of: ischemic stroke, epilepsy, trauma, Parkinson's disease, Alzheimer's disease, multiple sclerosis, mesial temporal sclerosis, Huntington's disease, and AIDS dementia complex.

* * * * *

UNITED STATES PATENT AND TRADEMARK OFFICE
CERTIFICATE OF CORRECTION

| | | |
|---|---|---|
| PATENT NO. | : 9,447,075 B2 | |
| APPLICATION NO. | : 14/236041 | |
| DATED | : September 20, 2016 | |
| INVENTOR(S) | : Gregory D. Cuny et al. | |

It is certified that error appears in the above-identified patent and that said Letters Patent is hereby corrected as shown below:

On the Title Page

On first page, Column 2 (Other Publications), Line 4, delete "ofthe" and insert -- of the --, On first page, Column 2 (Other Publications), Line 8, delete "dimethylmorpholino)" and insert -- dimethylmorpholine) --, On first page, Column 2 (Other Publications), Line 23, delete "elecfron" and insert -- electron --, On first page, Column 2 (Other Publications), Line 36, delete "Pshychiatry," and insert -- Psychiatry, --, In the Claims In Column 34, Line 59, in Claim 1, delete "(a)" and insert -- (a), --, In Column 34, Line 65, in Claim 1, delete "$C_{2-8}$" and insert -- $C_2$-$C_8$ --, In Column 34, Line 65, in Claim 13, delete "2, 6-dimethylphenyl," and insert -- 2,6-dimethylphenyl, --, In Column 34, Line 66, in Claim 13, delete "2, 4-dimethylphenyl," and insert -- 2,4-dimethylphenyl, --, In Column 34, Line 67, in Claim 13, delete "2, 6-dichlorophenyl," and insert -- 2,6-dichlorophenyl, --, In Column 35, Line 18, in Claim 1, delete "$C_1$-$C_6$ haloalkyl" and insert -- and $C_1$-$C_6$ haloalkyl --, Signed and Sealed this
Seventh Day of February, 2017

Michelle K. Lee
*Director of the United States Patent and Trademark Office*

CERTIFICATE OF CORRECTION (continued)
U.S. Pat. No. 9,447,075 B2

In Column 36, Line 64, in Claim 13, delete "2,4,6,-trimethylphenyl," and insert
-- 2,4,6-trimethylphenyl, --, In Column 36, Line 9 (approx.), in Claim 13, delete "2,4,6,-trifluorophenyl," and insert
-- 2,4,6-trifluorophenyl, --, In Column 36, Line 12 (approx.), in Claim 13, delete "3 -methylphenyl," and insert
-- 3-methylphenyl, --, In Column 36, Line 13 (approx.), in Claim 13, delete "1 -yloxy)phenyl," and insert
-- 1-yloxy)phenyl, --.